United States Patent
Bosch et al.

(10) Patent No.: US 6,428,814 B1
(45) Date of Patent: *Aug. 6, 2002

(54) BIOADHESIVE NANOPARTICULATE COMPOSITIONS HAVING CATIONIC SURFACE STABILIZERS

(75) Inventors: H. William Bosch; Eugene R. Cooper; Simon L. McGurk, all of King of Prussia, PA (US)

(73) Assignee: Elan Pharma International Ltd., Shannon County Clare (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/414,159

(22) Filed: Oct. 8, 1999

(51) Int. Cl.[7] .................................................. A61K 9/50
(52) U.S. Cl. ...................................... 424/501; 424/502
(58) Field of Search .............................. 424/489, 501, 424/502

(56) References Cited

U.S. PATENT DOCUMENTS

| | | | |
|---|---|---|---|
| 4,783,484 A | 11/1988 | Violante et al. | 514/535 |
| 4,826,689 A | 5/1989 | Violanto et al. | |
| 4,997,454 A | 3/1991 | Violante et al. | 23/305 |
| 5,145,684 A | 9/1992 | Liversidge et al. | 424/489 |
| 5,298,262 A | 3/1994 | Na et al. | 424/489 |
| 5,326,552 A | 7/1994 | Na et al. | 424/4 |
| 5,336,507 A | 8/1994 | Na et al. | 424/489 |
| 5,346,702 A | 9/1994 | Na et al. | 424/490 |
| 5,399,363 A | 3/1995 | Liversidge et al. | 424/490 |
| 5,429,824 A | 7/1995 | June | 424/489 |
| 5,447,710 A | 9/1995 | Na et al. | 424/9.455 |
| 5,470,583 A | 11/1995 | Na et al. | 424/489 |
| 5,510,118 A | 4/1996 | Bosch et al. | 424/489 |
| 5,518,187 A | 5/1996 | Bruno et al. | 241/5 |
| 5,565,188 A | 10/1996 | Wong et al. | 424/9.411 |
| 5,569,448 A | 10/1996 | Wong et al. | 424/9.45 |
| 5,580,579 A | 12/1996 | Ruddy et al. | 424/489 |
| 5,587,143 A | 12/1996 | Wong | 424/9.1 |
| 5,591,456 A | 1/1997 | Franson et al. | 424/494 |
| 5,593,657 A | 1/1997 | Ruddy et al. | 424/9.41 |
| 5,622,938 A | 4/1997 | Wong | 514/35 |
| 5,662,883 A | 9/1997 | Bagchi et al. | 424/9.4 |
| 5,665,331 A | 9/1997 | Bagchi et al. | 424/9.45 |

(List continued on next page.)

FOREIGN PATENT DOCUMENTS

| | | |
|---|---|---|
| EP | 275 796 | 7/1988 |
| EP | 315 589 | 5/1989 |
| EP | 461 079 | 12/1991 |
| EP | 549 524 | 6/1993 |
| EP | 0 577 215 | 1/1995 |
| WO | 91/10653 | 7/1991 |
| WO | 97/35603 | 10/1997 |
| WO | 98/07414 | 2/1998 |
| WO | 00/18374 | 4/2000 |
| WO | 00/53164 | 9/2000 |
| WO | 01/17546 | 3/2001 |

*Primary Examiner*—Carlos Azpuru
(74) *Attorney, Agent, or Firm*—Foley & Lardner

(57) ABSTRACT

Bioadhesive nanoparticulate compositions, comprising active agent particles and one or more cationic surface stabilizers, are described. The cationic surface stabilizers prevent aggregation of the nanoparticles and increase bioadhesion of the nanoparticles to biological substrates, such as an insect, teeth, bone, nails, chitin, feathers, scales, mucous, skin, hair, plant tissue, etc. The particles may consist of pharmacologically active compounds (e.g., drug compounds for human or veterinary use), agricultural chemicals (pesticides, herbicides, fertilizers, and the like), cosmetic agents, consumer products (coloring agents, flavors, or fragrances), or other materials which function by interacting with biological substrates. In addition, the invention relates to methods of preparing and using such bioadhesive nanoparticulate compositions.

27 Claims, 26 Drawing Sheets

U.S. PATENT DOCUMENTS

Figure 1:
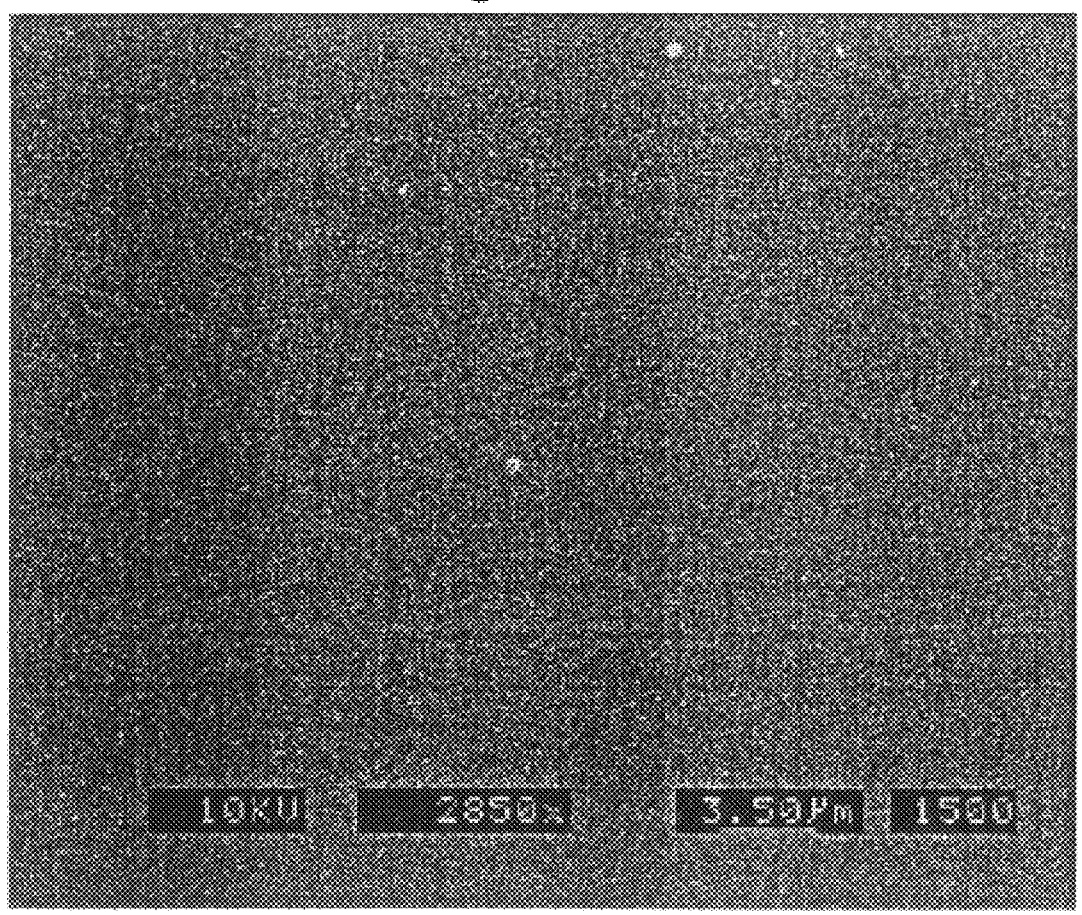

| | | |
|---|---|---|
| 5,718,388 A | 2/1998 | Czekai et al. .................. 241/21 |
| 5,741,522 A | 4/1998 | Violante et al. ............ 424/489 |
| 5,766,635 A | 6/1998 | Spenleuhauer et al. ..... 424/489 |
| 5,776,496 A | 7/1998 | Violante et al. ............ 424/489 |
| 5,862,999 A | 1/1999 | Czekai et al. .................. 241/21 |
| 5,912,219 A | 6/1999 | Carrie et al. ................ 510/238 |
| 5,929,015 A | 7/1999 | Lagnemo et al. ........... 510/378 |
| 5,929,024 A | 7/1999 | Stringer et al. ............ 510/504 |
| 5,932,193 A | 8/1999 | Lopez et al. .................. 424/52 |
| 5,932,202 A | 8/1999 | Guskey et al. ........... 424/70.19 |
| 5,932,253 A | 8/1999 | Trinh et al. .................. 424/719 |
| 5,932,404 A | 8/1999 | Chen et al. .................. 430/512 |
| 5,932,535 A | 8/1999 | Neuss et al. .................. 510/535 |
| 5,935,271 A | 8/1999 | Lappas et al. .................. 8/137 |
| 5,935,272 A | 8/1999 | Mahaffey, Jr. et al. .......... 8/403 |
| 5,935,561 A | 8/1999 | Inman et al. ............ 424/70.19 |
| 5,935,908 A | 8/1999 | Farooq et al. ............... 504/281 |
| 5,935,920 A | 8/1999 | Geke et al. .................. 510/245 |
| 5,935,921 A | 8/1999 | Meunier ..................... 510/247 |

Control Mucin Sample

Interaction of Naproxen Formulations with Mucin

Naproxen + PVP (k29/32)

Naproxen + PMMTMABr

Control Hair Sample
Figure 3A
Figure 3B
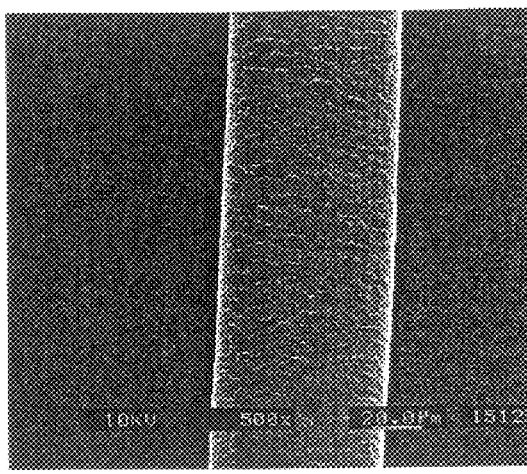
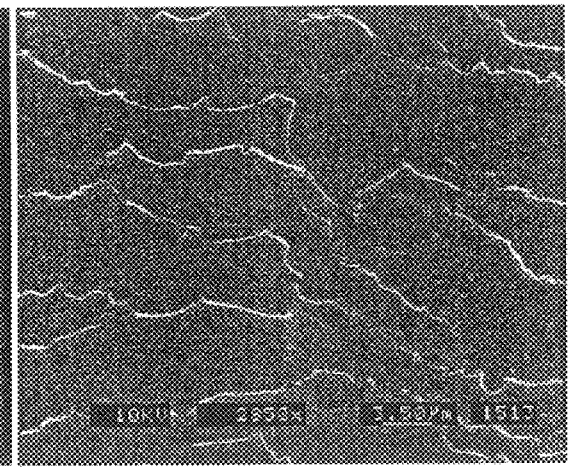

Interaction of Naproxen Formulations with Hair
Figure 4A
Figure 4B
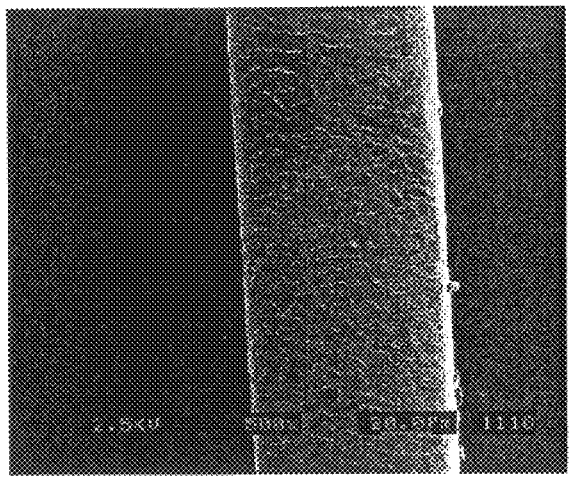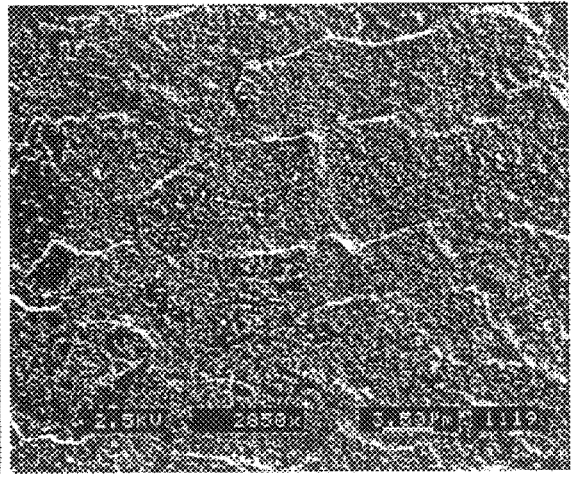
Naproxen + PMMTMABr

Interaction of Naproxen Formulations with Hair

Naproxen + PVP (k29/32)

Control Plant Sample

Interaction of Naproxen Formulations with Plant Tissue
Figure 7A
Figure 7B
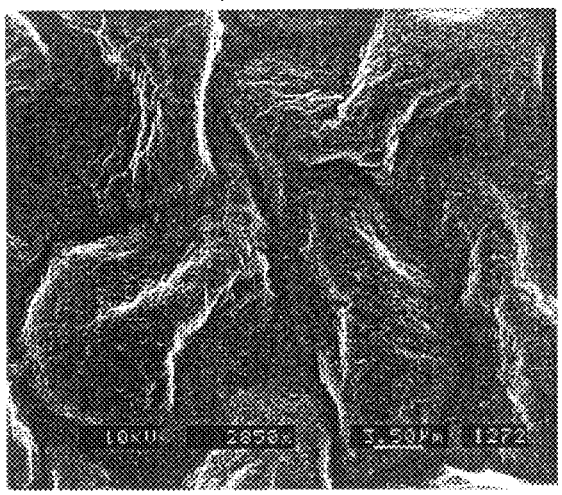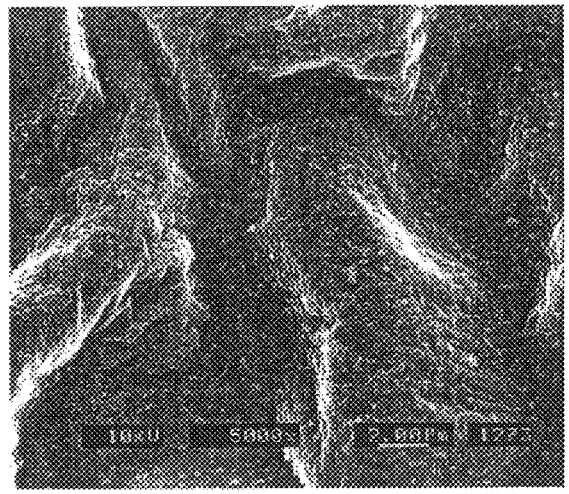
Naproxen + PMMTMABr

Interaction of Naproxen Formulations with Plant Tissue

Naproxen + PVP (k29/32)

Interaction of Cyclosporin Formulations with Mucin

Cyclosporin + F88 + SLS

Cyclosporin + F88 + HDMAB

Interaction of Cyclosporin Formulations with Hair

Cyclosporin + F88 + HDMAB

Interaction of Cyclosporin Formulations with Hair
Figure 11A
Figure 11B
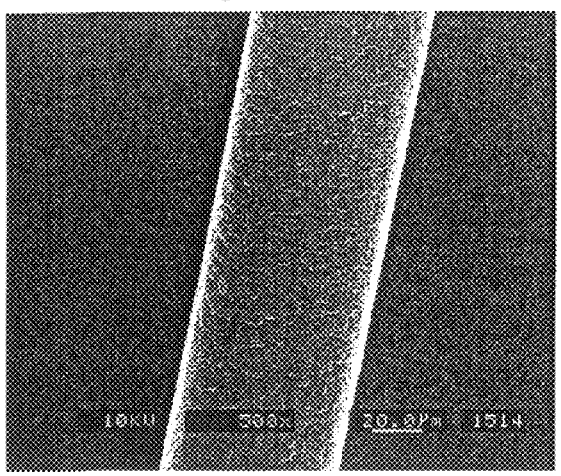
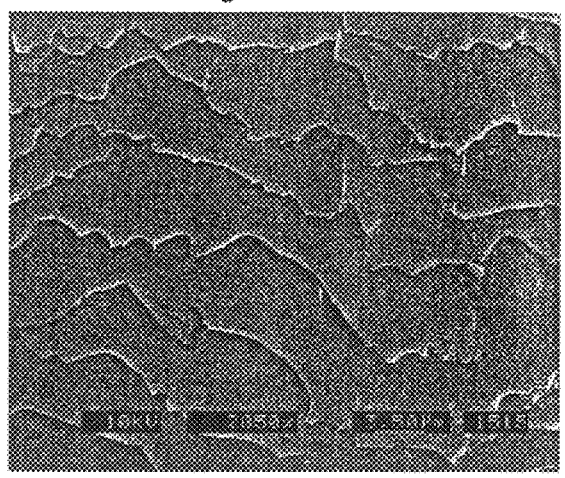
Cyclosporin + F88 + SLS

Interaction of Cyclosporin Formulations with Plant Tissue

Cyclosporin + F88 + SLS

Cyclosporin + F88 + HDMAB

Interaction of TA Formulations with Mucin

TA + HPC-sl + SLS

TA + HPC-sl + BKC

Interaction of TA Formulations with Hair
Figure 14A
Figure 14B
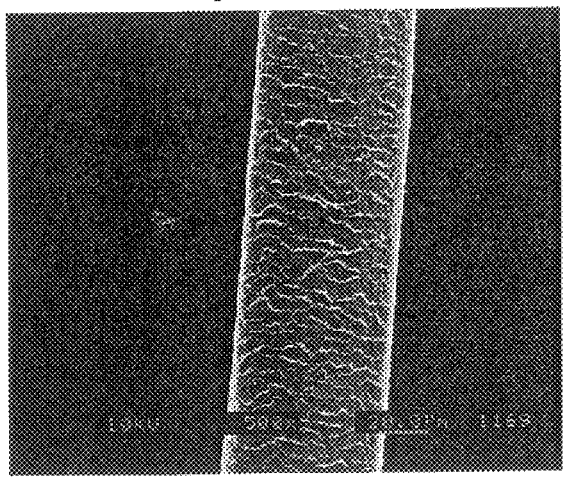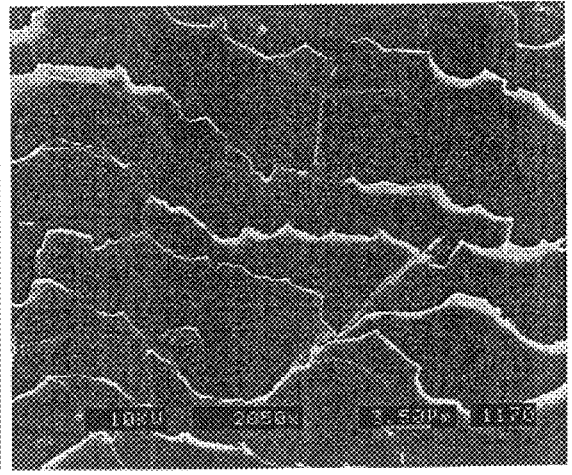
TA + HPC-sl + SLS

Interaction of TA Formulations with Hair
Figure 15A
Figure 15B
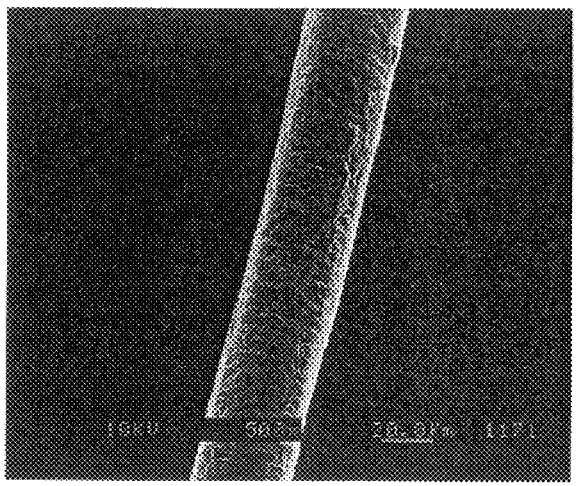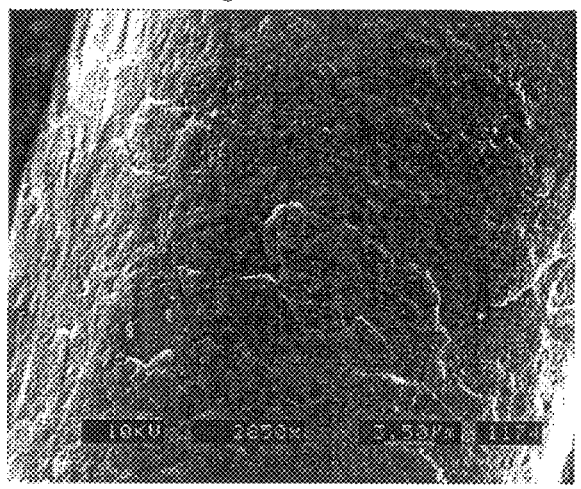
TA + HPC-sl + BKC Control Human Allograft Sample
Figure 16A
Figure 16B
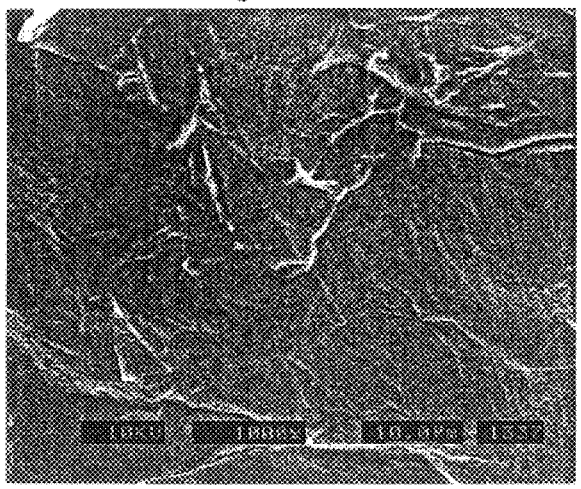
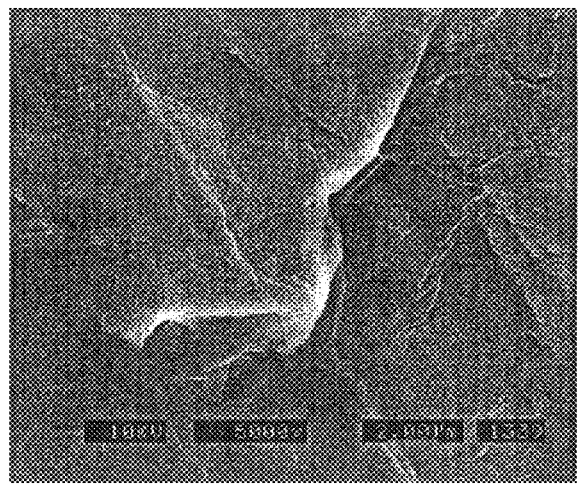

Interaction of WIN68209 Formulations with Allograft Skin

WIN68209 + F108

Interaction of WIN68209 Formulations with Allograft Skin

WIN68209 + PVPDMAEM

Interaction of Unmilled Naproxen (22μm) with Mucin Surface

Naproxen + PMMTMABr

Naproxen + PVP (k29/32)

Interaction of Unmilled Naproxen (22μm) with Human Hair

Naproxen + PMMTMABr

Interaction of Unmilled Naproxen (22μm) with Human Hair

Naproxen + PVP (k29/32)

Interaction of Unmilled Naproxen (22μm) with Plant Tissue

Naproxen + PMMTMABr

Naproxen + PVP (k29/32)

Interaction of Micronized Naproxen (6μm) with Mucin Surface

Naproxen + PMMTMABr

Naproxen + PVP (k29/32)

Interaction of Micronized Naproxen (6μm) with Human Hair
Figure 24A
Figure 24B
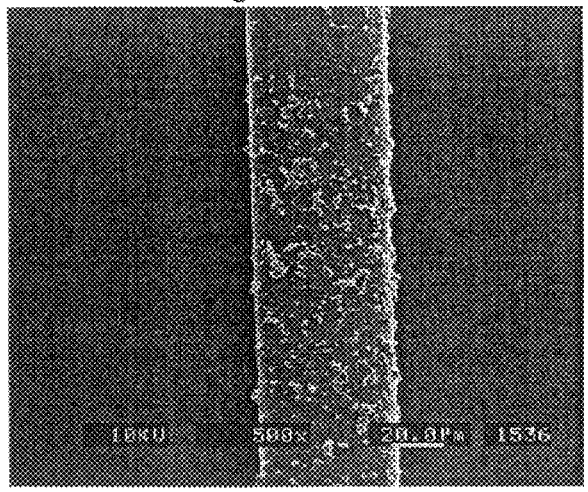
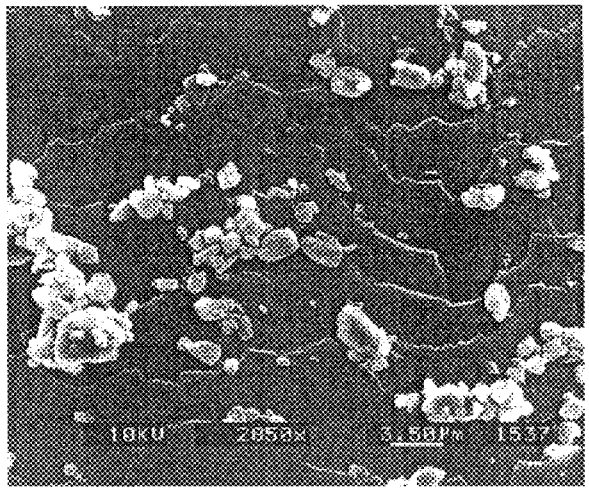
Naproxen + PMMTMABr

Interaction of Micronized Naproxen (6μm) with Human Hair

Naproxen + PVP (k29/32)

Interaction of Micronized Naproxen (6μm) with Plant Tissue
Figure 26A
Figure 26B
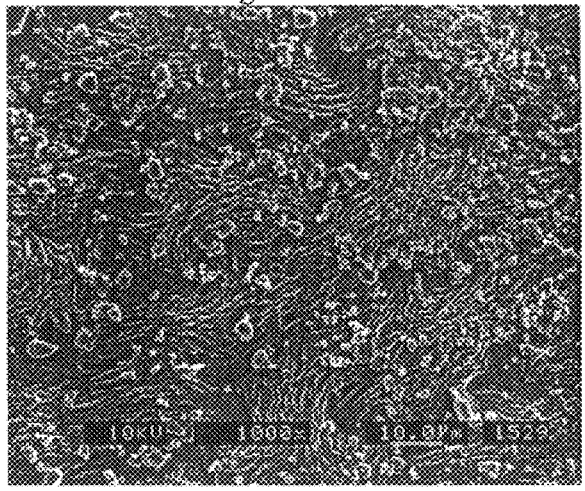
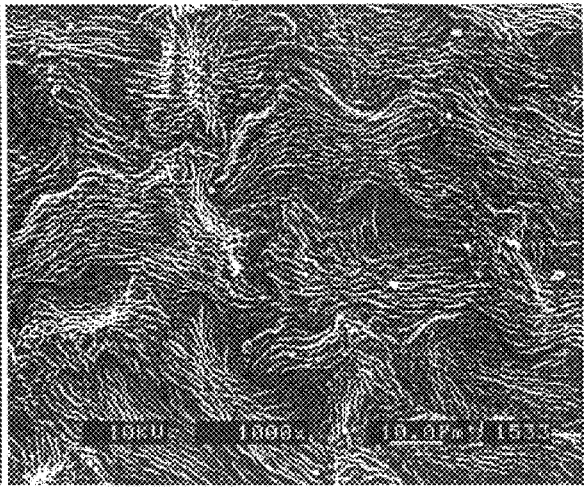
Naproxen + PMMTMABr
Naproxen + PVP (k29/32)

BIOADHESIVE NANOPARTICULATE COMPOSITIONS HAVING CATIONIC SURFACE STABILIZERS

BACKGROUND OF THE INVENTION

1. Field of the Invention

This invention relates to nanoparticulate compositions comprising particles of an active agent and one or more cationic surface stabilizers adsorbed to the surface of the active agent. The nanoparticulate compositions have superior adhesion properties to biological surfaces, such as mucous, skin, hair, plant tissue, etc.

2. Description of the Related Art

Nanoparticulate compositions, which were first described in U.S. Pat. No. 5,145,684 ("the '684 Patent"), comprise a poorly soluble crystalline drug and a non-crosslinked surface stabilizer adsorbed to the surface of the drug. Nanoparticulate compositions are superior to macro-sized particulate drug formulations as nanoparticulate drug formulations can exhibit reduced toxicity and enhanced efficacy (U.S. Pat. No. 5,399,363), enhanced bioavailability (U.S. Pat. No. 5,662,883), and enhanced stability (U.S. Pat. No. 5,665,331). The '684 patent teaches that ionic and non-ionic surface stabilizers are preferred for nanoparticulate compositions.

The '684 patent describes a method of screening drugs to identify useful surface stabilizers that enable the production of a nanoparticulate composition. Not all surface stabilizers will function to produce a stable, non-agglomerated nanoparticulate composition for all drugs. Moreover, known surface stabilizers may be unable to produce a stable, non-agglomerated nanoparticulate composition for certain drugs. Thus, there is a need in the art to identify new surface stabilizers useful in making nanoparticulate compositions. Additionally, such new surface stabilizers may have superior properties over prior known surface stabilizers.

Exemplary known surface stabilizers useful in stabilizing and preventing the aggregation of nanoparticulate active agents are described in the '684 patent. Known and particularly preferred surface stabilizers for nanoparticulate compositions include tyloxapol (U.S. Pat. No. 5,429,824), polyalkylene block copolymers (U.S. Pat. No. 5,565,188), sulfated non-ionic block copolymers (U.S. Pat. No. 5,569,448), high molecular weight, linear, poly(ethylene oxide) polymers (U.S. Pat. No. 5,580,579), butylene oxide-ethylene oxide block copolymers (U.S. Pat. No. 5,587,143), hydroxypropyl cellulose (U.S. Pat. No. 5,591,456), and sugar based surface stabilizers (U.S. Pat. No. 5,622,938).

Several prior art methods for minimizing nanoparticle aggregation following heat sterilization utilize non-ionic surface stabilizers and cloud point modifiers. Such methods include adding an anionic or cationic cloud point modifier to a nanoparticulate composition (U.S. Pat. No. 5,298,262); adding a non-ionic surface stabilizer and a non-ionic cloud point modifier to a nanoparticulate composition (U.S. Pat. No. 5,346,702); adding a non-ionic surface stabilizer and a charged phospholipid as a cloud point modifier to a nanoparticulate composition (U.S. Pat. No. 5,470,583); and adding a non-ionic surface modifier and a charged phospholipid to a nanoparticulate composition (U.S. Pat. Nos. 5,336,507 and 5,470,583).

Anionic and non-ionic surface stabilizers for nanoparticulate compositions have also been described. For example, U.S. Pat. No. 5,593,657 discloses nanoparticulate x-ray contrast compositions comprising anionic and non-ionic surface stabilizers. The nanoparticulate compositions adhere to the mucosal surface of the gastrointestinal tract (GIT), allowing for diagnostic examination of the GIT. U.S. Pat. No. 5,326,552 describes a nanoparticulate x-ray contrast composition having a high molecular weight non-ionic surface stabilizer and a cloud point modifier. In addition, U.S. Pat. No. 5,447,710 describes nanoparticulate x-ray contrast compositions having high molecular weight non-ionic surface stabilizers and a cloud point modifier.

Cationic surfactants are used in a wide variety of products and applications. For example, they are often used in cleaning, degreasing, and detergent compositions (U.S. Pat. Nos. 5,935,921, 5,935,272, and 5,912,219), liquid cleansers, bar soaps (U.S. Pat. No. 5,935,920), pesticides (U.S. Pat. No. 5,935,908), hair care products, such as shampoos and conditioners (U.S. Pat. Nos. 5,935,561, 5,932,535, and 5,932,202), laundry detergent (U.S. Pat. Nos. 5,935,271 and 5,929,024), photographic materials (U.S. Pat. No. 5,932,404), fabric softening compositions (U.S. Pat. No. 5,932,253), toothpaste compositions (U.S. Pat. No. 5,932,193), bleaching agents (U.S. Pat. No. 5,929,015), textile treatment compositions, automatic dishwashing detergent powders, cosmetics, environmental remediation (contaminated soil/groundwater remediation), enhanced oil recovery, and in medical applications, such as application to the lungs of premature infants.

There is a need in the art for effective, stable compositions having excellent adhesion properties to biological surfaces. The present invention satisfies these needs.

SUMMARY OF THE INVENTION

The present invention is directed to stable bioadhesive nanoparticulate compositions comprising an active agent and at least one cationic surface stabilizer. The active agent can be either crystalline, semi-crystalline, or amorphous, or liquid at or near room temperature. The active agent particles can be dissolved or dispersed in a liquid medium or used in dry form.

In one embodiment, described are stable bioadhesive nanoparticulate compositions comprising particles of a poorly water-soluble active agent and, adsorbed to the surface of the agent, at least one cationic surface stabilizer. The active agent can be either crystalline, semi-crystalline, or amorphous. The active agent particles of the nanoparticulate composition have an effective average particle size of less than about 4000 nm. The active agent particles can be dispersed in a liquid medium or used in dry form.

In yet another embodiment, described are stable bioadhesive nanoparticulate compositions comprising particles of a water-soluble active agent and, adsorbed to the surface of the agent, at least one cationic surface stabilizer. The active agent can be either crystalline, semi-crystalline, or amorphous. The active agent particles of the nanoparticulate composition have an effective average particle size of less than about 4000 nm. The active agent particles can be dispersed in a liquid medium or used in dry form.

In a further embodiment, described are stable bioadhesive nanoparticulate compositions comprising liquid particles of a poorly water-soluble active agent and, adsorbed to the surface of the liquid particles, at least one cationic surface stabilizer. The active agent is in a liquid state at or near room temperature. In this embodiment, the nanoparticulate composition is in the form of an emulsion. The active agent emulsion droplets of the nanoparticulate composition have an effective average particle size of less than about 4000 nm. The active agent emulsion droplets are dispersed in a liquid medium in which they are poorly soluble, such as water.

In a further embodiment, described are stable bioadhesive nanoparticulate compositions comprising liquid particles of a water-soluble active agent and, adsorbed to the surface of the liquid particles, at least one cationic surface stabilizer. The active agent is in a liquid state at or near room temperature. In this embodiment, the nanoparticulate composition is in the form of an emulsion. The active agent emulsion droplets of the nanoparticulate composition have an effective average particle size of less than about 4000 nm. The active agent emulsion droplets are dispersed in a liquid medium in which they are poorly soluble, such as mineral oil, vegetable oils (corn, safflower, olive, etc.), or a hydrocarbon.

Also described are stable bioadhesive nanoparticulate compositions comprising active agent particles dissolved or dispersed in liquid droplets of a poorly water-soluble liquid and, adsorbed to the surface of the liquid droplets, at least one cationic surface stabilizer. For this composition, the liquid droplets comprising active agent are dispersed in a liquid medium in which they are poorly soluble, such as water. In addition, the liquid droplets comprising active agent have an effective average particle size of less than about 4000 nm.

Yet another composition encompassed by the invention is a stable bioadhesive nanoparticulate composition comprising active agent particles dissolved or dispersed in liquid droplets of a water-soluble liquid and, adsorbed to the surface of the liquid droplets, at least one cationic surface stabilizer. For this composition, the liquid droplets comprising active agent are dispersed in a liquid medium in which they are poorly soluble, such as mineral oil, vegetable oils (corn, safflower, olive, etc.), or a hydrocarbon. In addition, the liquid droplets comprising active agent have an effective average particle size of less than about 4000 nm.

Another aspect of the invention is directed to pharmaceutical compositions comprising one or more nanoparticulate compositions of the invention. The pharmaceutical composition preferably comprises a nanoparticulate composition described above and a pharmaceutically acceptable carrier, as well as any desired excipients.

This invention further discloses methods of making nanoparticulate compositions according to the invention. A first method comprises contacting a nanoparticulate active agent with at least one cationic surface stabilizer for a time and under conditions sufficient to provide a stable nanoparticulate composition in which the cationic surface stabilizer is adsorbed to the surface of the active agent particles. The cationic surface stabilizer can be contacted with the active agent either before, during, or after size reduction of the active agent. The agent can be either crystalline, semi-crystalline, amorphous, or a mixture thereof. The active agent particles of the nanoparticulate composition have an effective average particle size of less than about 4000 nm. The effective average particle size can be achieved by wet milling techniques (such as described in the '684 patent), by controlled precipitation methods, by homogenization, or by other suitable size reduction methods.

In cases where the active agent is in a liquid state at or near room temperature, the nanoparticulate composition is in the form of an emulsion. In such cases, a method of making the emulsion comprises combining the liquid active agent with an emulsifying agent and a liquid non-solvent and processing the resultant mixture with a homogenizer, high-shear mixer, rotor-stator type device, Microfluidizer®, or other such equipment which is suitable for preparing emulsions and is well known to those skilled in the art. For this composition, the cationic surface stabilizer is adsorbed to the surface of the liquid active agent of the emulsion.

The invention also encompasses variations of this nanoparticulate emulsion formulation. For example, an active agent can be dissolved in a liquid droplet of an emulsion, or the active agent can be dispersed as a solid particle within a liquid droplet of an emulsion. In the first type of formulation, the liquid droplet in which the active agent is dissolved is dispersed within a liquid in which the liquid droplet is insoluble. In the second type of formulation, the active agent is dispersed within a liquid droplet of the emulsion; i.e., the active agent is insoluble in the liquid droplet of the emulsion. Moreover, the liquid droplets comprising the solid particles of the active agent are dispersed within a second liquid in which the liquid droplets are insoluble.

For these types of emulsion formulations, if the active agent nanoparticles are insoluble within the liquid droplets of the emulsion, then at least one cationic surface stabilizer is adsorbed to the surface of the active agent nanoparticles, the surface of the liquid emulsion droplets comprising the active agent particles, or a combination thereof. If, however, the active agent nanoparticles are soluble within the liquid droplets of the emulsion, then at least one cationic surface stabilizer is adsorbed to the surface of the liquid droplets comprising the active agent nanoparticles. The cationic surface stabilizers may be present during the emulsification process or may be added after the emulsion has been formed.

In a third method, aqueous nanoparticulate dispersions of water-soluble active agents may be prepared by encapsulating the active agent particles with a suitable coating and then dispersing them in water. The water-soluble nanoparticles may be prepared by wet milling in liquid nonsolvents, controlled precipitation, or other methods known to those in the art. After removal of the nonsolvents by evaporation, the nanoparticles may be treated with a protective coating, such as ethylcellulose, and subsequently dispersed in an aqueous vehicle. At least one cationic surface stabilizer is adsorbed to the encapsulated nanoparticles.

The present invention is further directed to methods of treatment comprising administering to an animal in need a therapeutically effective amount of a nanoparticulate therapeutic active agent/cationic surface stabilizer composition according to the invention. The active agent can be administered via any biological surface of the animal.

Yet another aspect of the invention is directed to the application of the described bioadhesive nanoparticulate compositions to any biological surface of an animal. Such application encompasses, for example, the application of nanoparticulate compositions useful as cosmetics, perfumes, shampoos, cleansers, moisturizers, deodorants, topical creams, ointments, nail polish, hair cosmetic compositions, etc.

The compositions of the invention can also be applied to plant tissue. Such methods include applying nanoparticulate compositions useful as fertilizers, pesticides, herbicides, etc. to a biological surface of a plant.

Both the foregoing general description and the following detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 1: A scanning electron micrograph shows a control mucin sample at 2850×magnification;

Figure 2A:
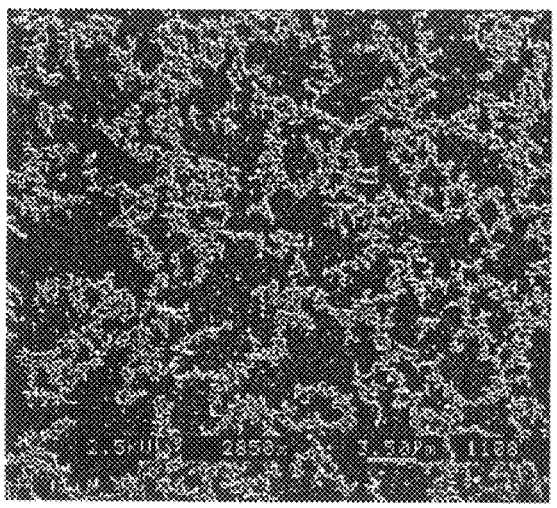
Figure 2B:
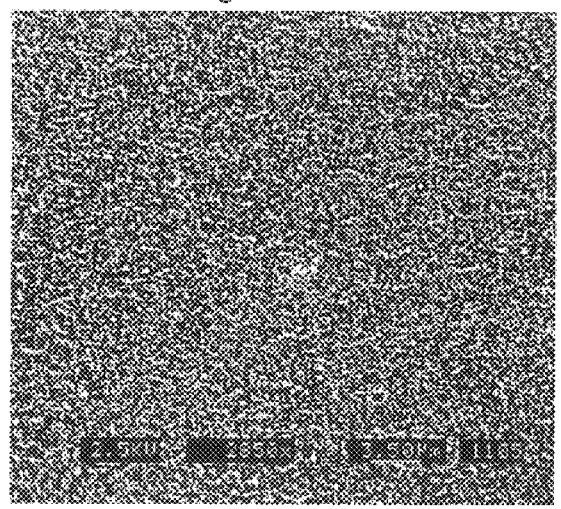
Figure 5A:
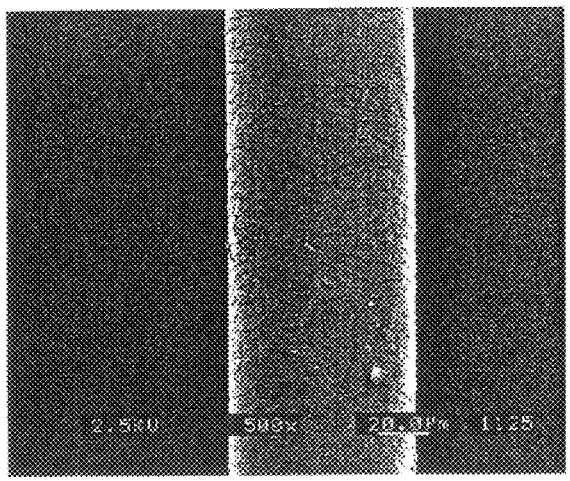
Figure 5B:
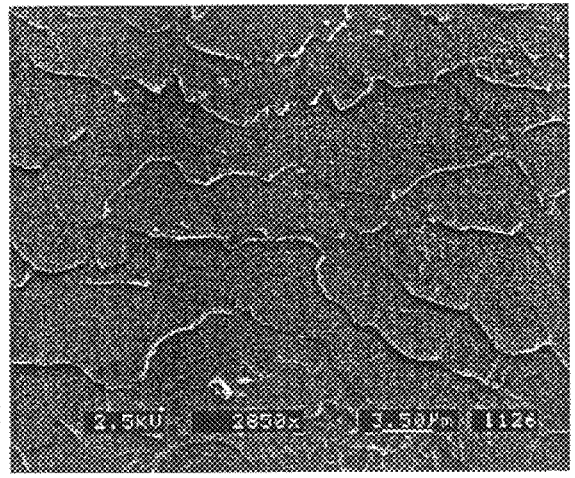
Figure 6A:
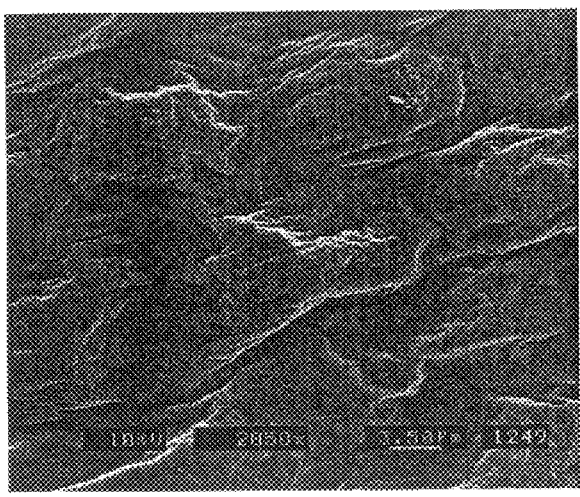
Figure 6B:
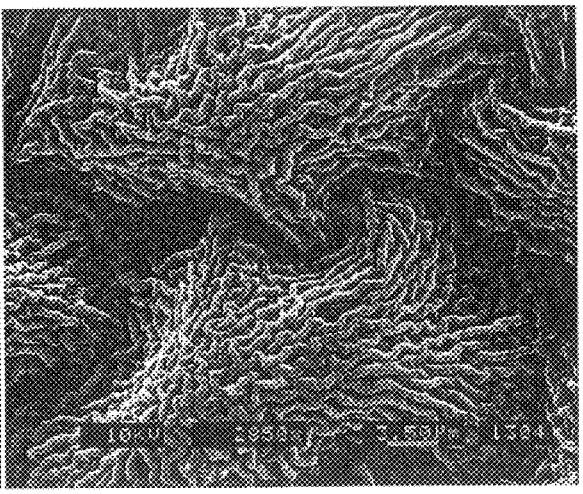
Figure 8A:
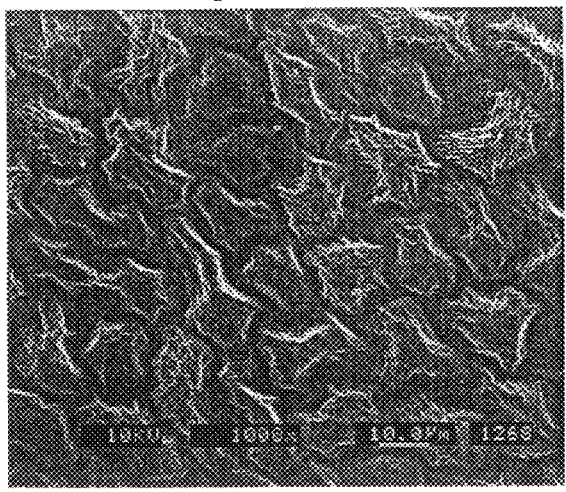
Figure 8B:
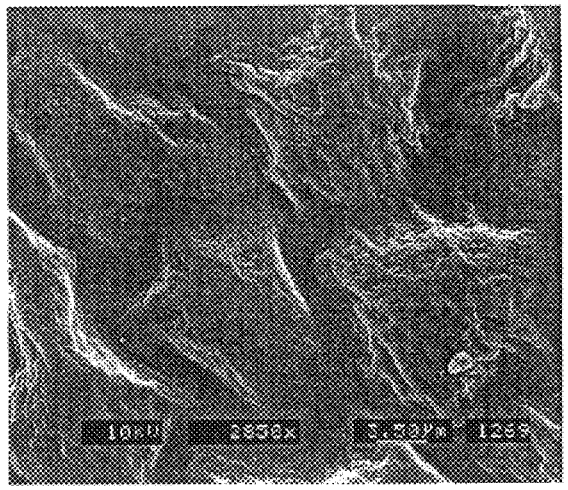
Figure 9A:
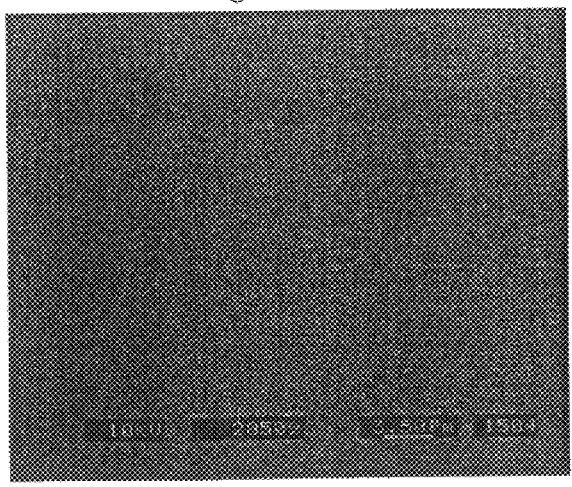
Figure 9B:
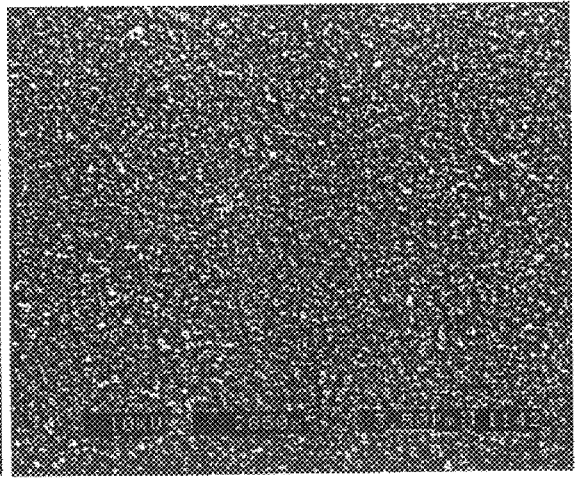
Figure 10A:
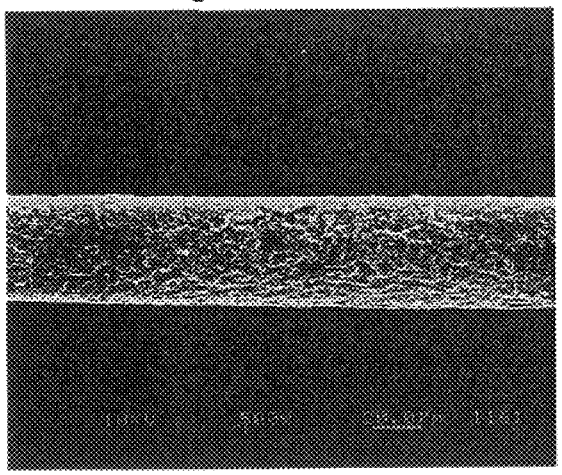
Figure 10B:
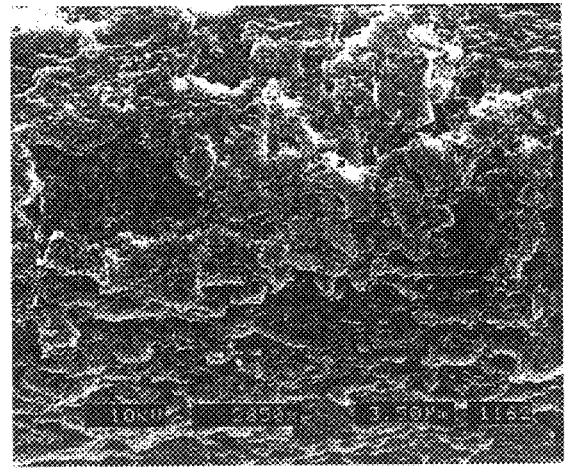
Figure 12A:
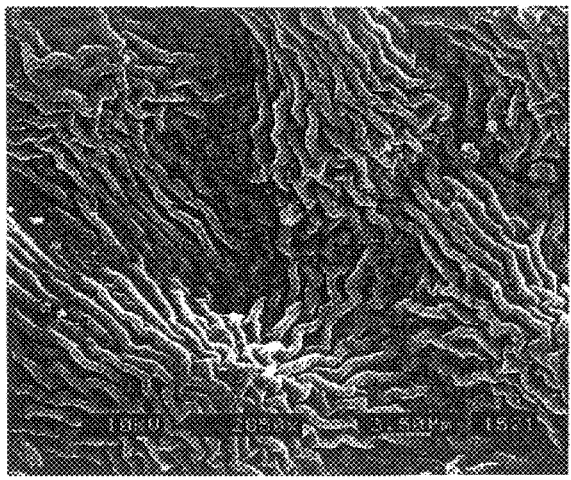
Figure 12B:
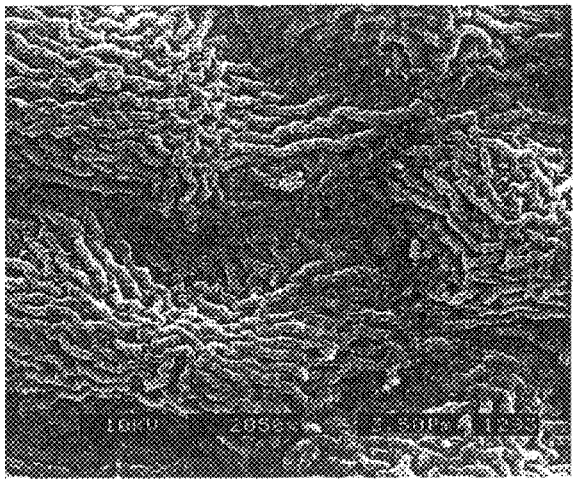
Figure 13A:
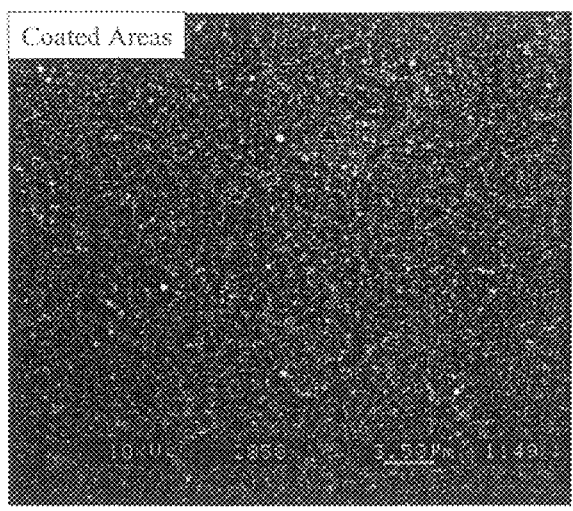
Figure 13B:
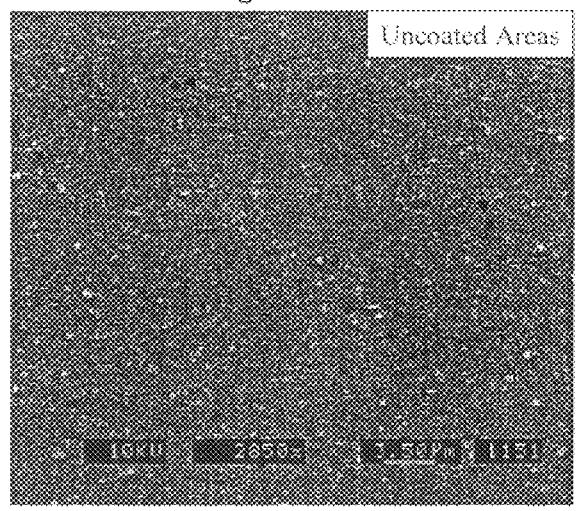
Figure 17A:
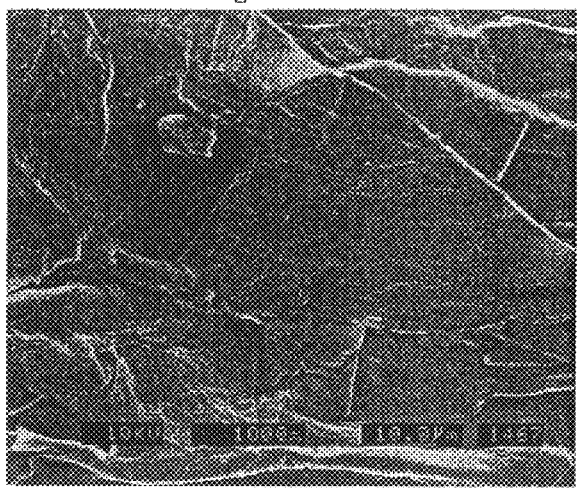
Figure 17B:
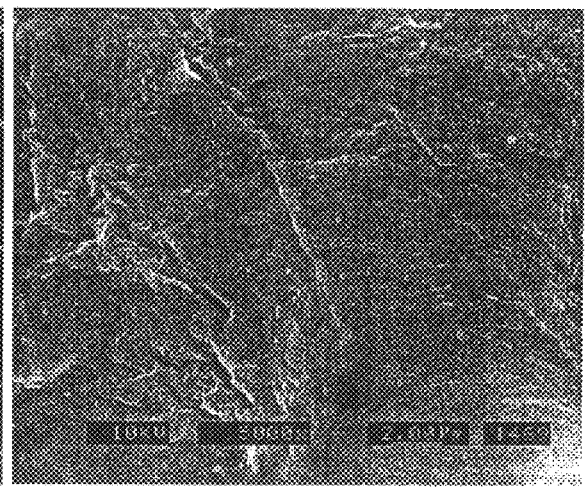
Figure 18A:
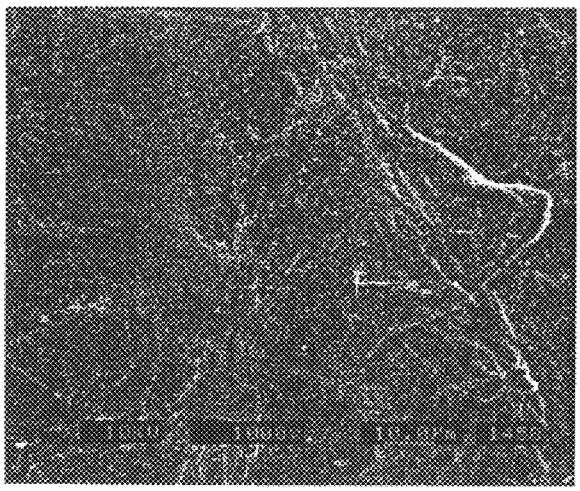
Figure 18B:
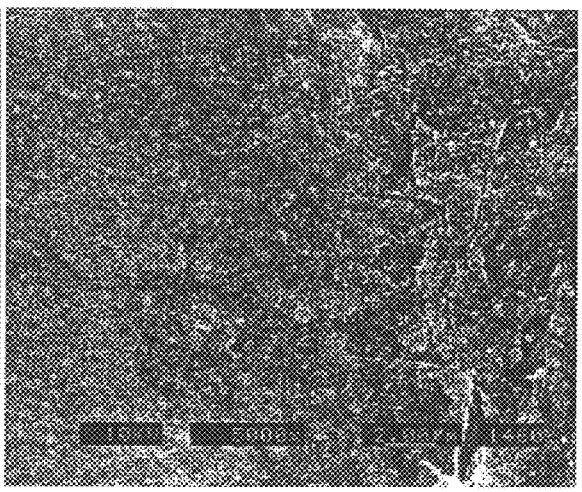
Figure 19A:
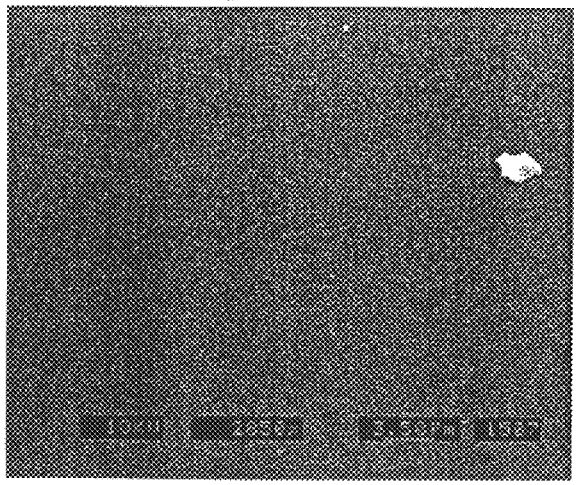
Figure 19B:
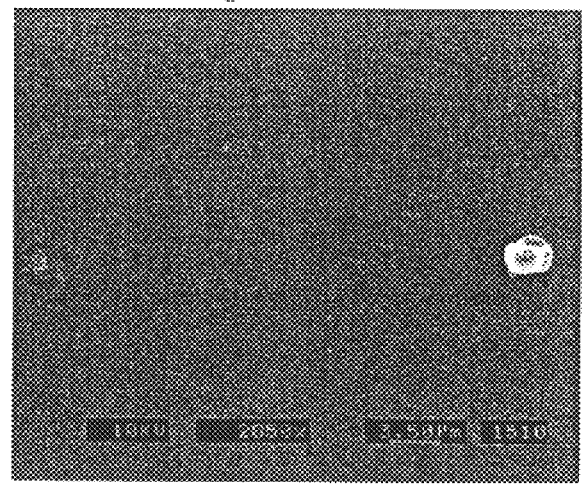
Figure 20A:
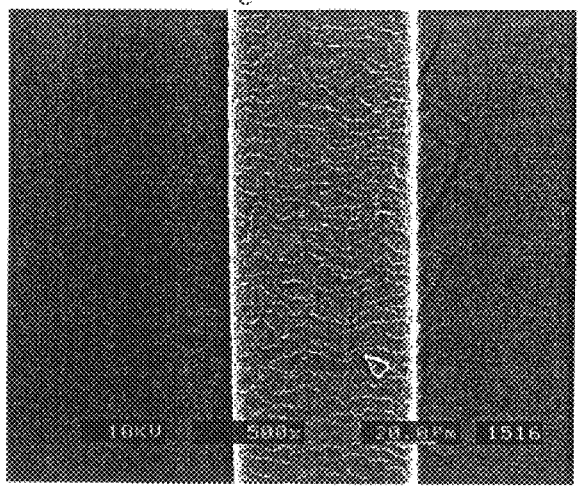
Figure 20B:
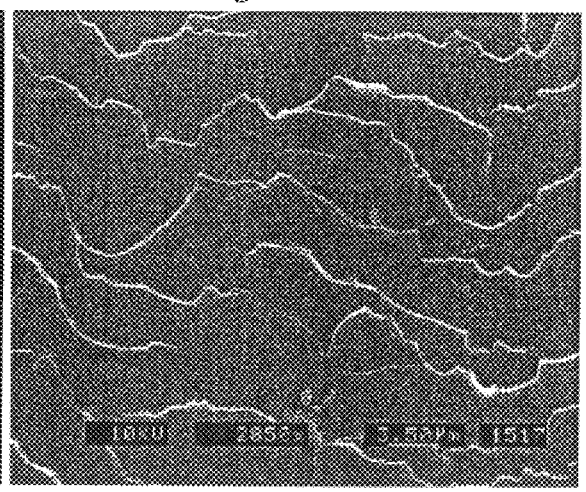
Figure 21A:
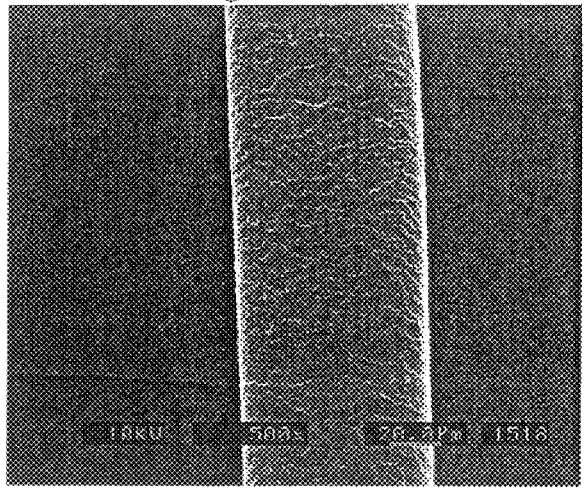
Figure 21B:
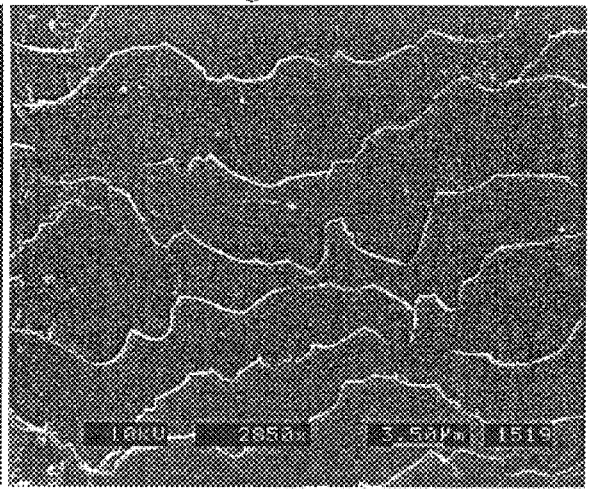
Figure 22A:
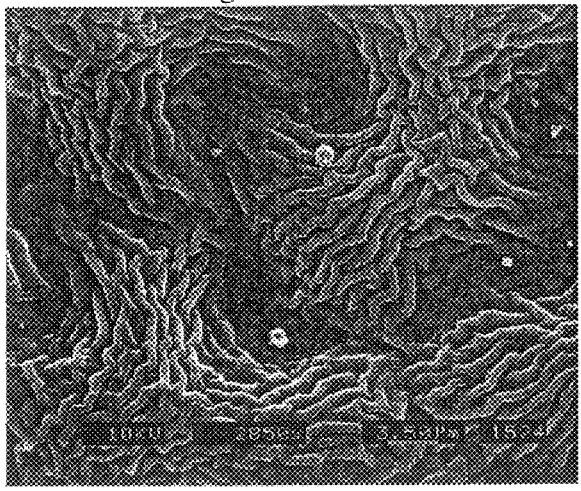
Figure 22B:
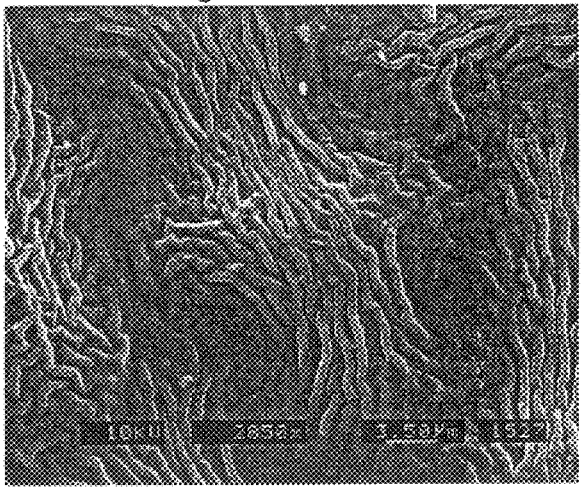
Figure 23A:
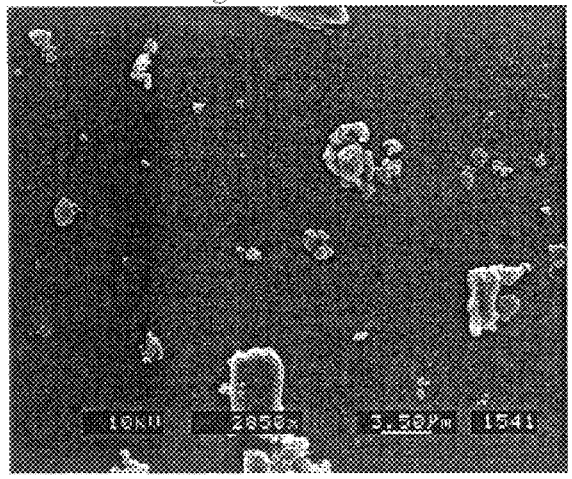

FIG. 2A: A scanning electron micrograph shows the interaction between mucin and a nanoparticulate naproxen formulation having as a surface stabilizer polyvinylpyrrolidone (PVP), which is a conventional non-cationic surface stabilizer, at 2850×magnification;

FIG. 2B: A scanning electron micrograph shows the interaction between mucin and a nanoparticulate naproxen formulation having as a surface stabilizer polymethylmethacrylate trimethylammoniumbromide (PMMTMABr), which is a cationic surface stabilizer, at 2850×magnification;

FIG. 3A: A scanning electron micrograph shows a control hair sample at 500×magnification;

FIG. 3B: A scanning electron micrograph shows a control hair sample at 2850×magnification;

FIG. 4A: A scanning electron micrograph shows the interaction between hair and a nanoparticulate naproxen formulation having as a surface stabilizer PMMTMABr at 500×magnification;

FIG. 4B: A scanning electron micrograph shows the interaction between hair and a nanoparticulate naproxen formulation having as a surface stabilizer PMMTMABr at 2850×magnification;

FIG. 5A: A scanning electron micrograph shows the interaction between hair and a nanoparticulate naproxen formulation having as a surface stabilizer PVP at 500× magnification;

FIG. 5B: A scanning electron micrograph shows the interaction between hair and a nanoparticulate naproxen formulation having as a surface stabilizer PVP at 2850× magnification;

FIG. 6A: A scanning electron micrograph shows a control plant sample at 500×magnification;

FIG. 6B: A scanning electron micrograph shows a control plant sample at 2850×magnification;

FIG. 7A: A scanning electron micrograph shows the interaction between plant tissue and a nanoparticulate naproxen formulation having as a surface stabilizer PMMTMABr at 2850×magnification;

FIG. 7B: A scanning electron micrograph shows the interaction between plant tissue and a nanoparticulate naproxen formulation having as a surface stabilizer PMMTMABr at 5000×magnification;

FIG. 8A: A scanning electron micrograph shows the interaction between plant tissue and a nanoparticulate naproxen formulation having as a surface stabilizer PVP at 1000×magnification;

FIG. 8B: A scanning electron micrograph shows the interaction between plant tissue and a nanoparticulate naproxen formulation having as a surface stabilizer PVP at 2850×magnification;

FIG. 9A: A scanning electron micrograph shows the interaction between mucin and a nanoparticulate cyclosporine formulation having as surface stabilizers Pluronic® F88 (BASF) and sodium lauryl sulfate; which are conventional non-cationic surface stabilizers, at 2850×magnification;

FIG. 9B: A scanning electron micrograph shows the interaction between mucin and a nanoparticulate cyclosporine formulation having as surface stabilizers Pluronic® F88 and HDMAB, which is a cationic surface stabilizer, at 2850×magnification;

FIG. 10A: A scanning electron micrograph shows the interaction between hair and a nanoparticulate cyclosporine formulation having as surface stabilizers Pluronic® F88 and HDMAB at 500×magnification;

FIG. 10B: A scanning electron micrograph shows the interaction between hair and a nanoparticulate cyclosporine formulation having as surface stabilizers Pluronic® F88 and HDMAB at 2850×magnification;

FIG. 11A: A scanning electron micrograph shows the interaction between hair and a nanoparticulate cyclosporine formulation having as surface stabilizers Pluronic® F88 and sodium lauryl sulfate at 500×magnification;

FIG. 11B: A scanning electron micrograph shows the interaction between hair and a nanoparticulate cyclosporine formulation having as surface stabilizers Pluronic® F88 and sodium lauryl sulfate at 2850×magnification;

FIG. 12A: A scanning electron micrograph shows the interaction between plant tissue and a nanoparticulate cyclosporine formulation having as surface stabilizers Pluronic® F88 and sodium lauryl sulfate at 2850× magnification;

FIG. 12B: A scanning electron micrograph shows the interaction between plant tissue and a nanoparticulate cyclosporine formulation having as surface stabilizers Pluronic® F88 and HDMAB at 2850×magnification;

FIG. 13A: A scanning electron micrograph shows the interaction between mucin and a nanoparticulate triamcinolone acetonide formulation having as surface stabilizers hydroxypropyl cellulose and sodium lauryl sulfate, which are conventional non-cationic surface stabilizers, at 2850× magnification;

FIG. 13B: A scanning electron micrograph shows the interaction between mucin and a nanoparticulate triamcinolone acetonide formulation having as surface stabilizers hydroxypropyl cellulose and benzalkonium chloride which is a cationic surface stabilizer, at 2850×magnification;

FIG. 14A: A scanning electron micrograph shows the interaction between hair and a nanoparticulate triamcinolone acetonide formulation having as surface stabilizers hydroxypropyl cellulose and sodium lauryl sulfate at 500× magnification;

FIG. 14B: A scanning electron micrograph shows the interaction between hair and a nanoparticulate triamcinolone acetonide formulation having as surface stabilizers hydroxypropyl cellulose and sodium lauryl sulfate at 2850× magnification;

FIG. 15A: A scanning electron micrograph shows the interaction between hair and a nanoparticulate triamcinolone acetonide formulation having as surface stabilizers hydroxypropyl cellulose and BKC at 500×magnification;

FIG. 15B: A scanning electron micrograph shows the interaction between hair and a nanoparticulate triamcinolone acetonide formulation having as surface stabilizers hydroxypropyl cellulose and BKC at 2850×magnification;

FIG. 16A: A scanning electron micrograph shows a control human allograft skin sample at 1000×magnification;

FIG. 16B: A scanning electron micrograph shows a control human allograft skin sample at 5000×magnification;

FIG. 17A: A scanning electron micrograph shows the interaction between human allograft skin and a nanoparticulate formulation of WIN68209, an x-ray contrast agent, having as surface stabilizer Pluronic® F108 at 1000× magnification;

FIG. 17B: A scanning electron micrograph shows the interaction between human allograft skin and a nanoparticulate formulation of WIN68209, an x-ray contrast agent, having as surface stabilizer Pluronic® F108 at 5000× magnification;

FIG. 18A: A scanning electron micrograph shows the interaction between human allograft skin and a nanoparticulate formulation of WIN68209, an x-ray contrast agent, having as surface stabilizer, polyvinylpyrrolidone-2-dimethylaminoethyl methacrylate dimethyl sulfate (PVPDMAEM) at 1000×magnification;

FIG. 18B: A scanning electron micrograph shows the interaction between human allograft skin and a nanoparticulate formulation of WIN68209, an x-ray contrast agent, having as surface stabilizer, polyvinylpyrrolidone-2-dimethylaminoethyl methacrylate dimethyl sulfate (PVPDMAEM) at 5000×magnification;

FIG. 19A: A scanning electron micrograph shows the interaction between mucin and an unmilled (about 22 μm) naproxen formulation having as a surface stabilizer PMMTMABr at 2850×magnification;

FIG. 19B: A scanning electron micrograph shows the interaction between mucin and an unmilled(about 22 μm) naproxen formulation having as a surface stabilizer PVP (K29/32) at 2850×magnification;

FIG. 20A: A scanning electron micrograph shows the interaction between hair and an unmilled(about 22 μm) naproxen formulation having as a surface stabilizer PMMTMABr at 500×magnification;

FIG. 20B: A scanning electron micrograph shows the interaction between hair and an unmilled(about 22 μm) naproxen formulation having as a surface stabilizer PMMTMABr at 2850×magnification;

FIG. 21A: A scanning electron micrograph shows the interaction between hair and an unmilled (about 22 μm) naproxen formulation having as a surface stabilizer PVP (K29/32) at 500×magnification;

FIG. 21B: A scanning electron micrograph shows the interaction between hair and an unmilled(about 22 μm) naproxen formulation having as a surface stabilizer PVP (K29/32) at 2850×magnification;

FIG. 22A: A scanning electron micrograph shows the interaction between plant tissue and an unmilled(about 22 μm) naproxen formulation having as a surface stabilizer PMMTMABr at 2850×magnification;

FIG. 22B: A scanning electron micrograph shows the interaction between plant tissue and an unmilled(about 22 μm) naproxen formulation having as a surface stabilizer PVP (K29/32) at 2850×magnification;

FIG. 23A: A scanning electron micrograph shows the interaction between mucin and a micronized (about 6 μm) naproxen formulation having as a surface stabilizer PMMTMABr at 2850×magnification.

Figure 23B:
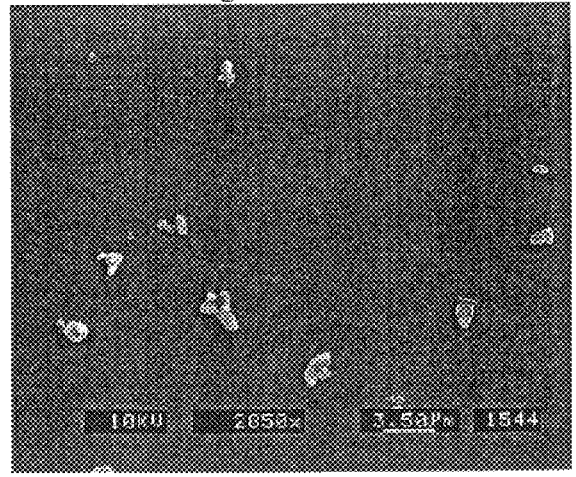

FIG. 23B: A scanning electron micrograph shows the interaction between mucin and a micronized (about 6 μm) naproxen formulation having as a surface stabilizer PVP at 2850×magnification.

Figure 25A:
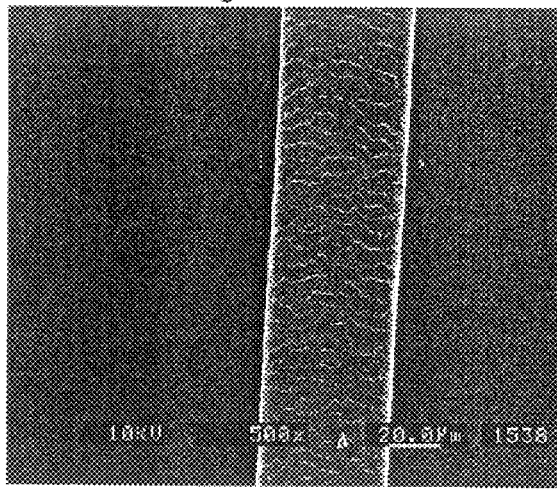
Figure 25B:
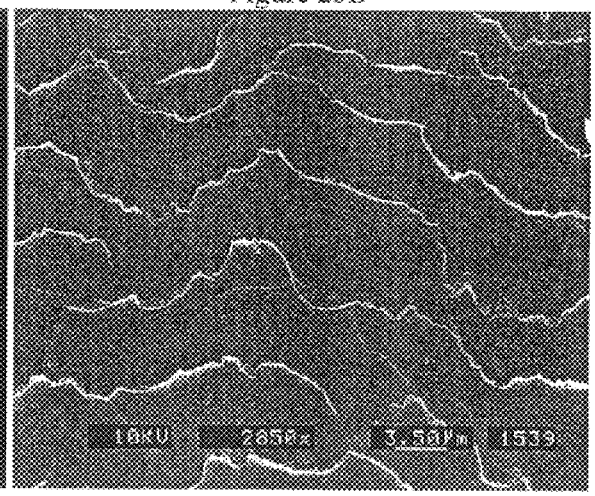

FIG. 24A: A scanning electron micrograph shows the interaction between hair and a micronized (about 6 μm) naproxen formulation having as a surface stabilizer PMMTMABr at 500×magnification;

FIG. 24B: A scanning electron micrograph shows the interaction between hair and a micronized (about 6 μm) naproxen formulation having as a surface stabilizer PMMTMABr at 2850×magnification;

FIG. 25A: A scanning electron micrograph shows the interaction between hair and a micronized (about 6 μm) naproxen formulation having as a surface stabilizer PVP (K29/32) at 500×magnification;

FIG. 25B: A scanning electron micrograph shows the interaction between hair and a micronized (about 6 μm) naproxen formulation having as a surface stabilizer PVP (K29/32) at 2850×magnification;

FIG. 26A: A scanning electron micrograph shows the interaction between plant tissue and a micronized (about 6 μm) naproxen formulation having as a surface stabilizer PMMTMABr at 1000×magnification; and FIG. 26B: A scanning electron micrograph shows the interaction between plant tissue and a micronized (about 6 μm) naproxen formulation having as a surface stabilizer PVP (K29/32) at 1000×magnification.

DETAILED DESCRIPTION OF THE INVENTION

The present invention is directed to the discovery that nanoparticulate compositions, comprising an active agent and having one or more cationic surface stabilizers adsorbed to the surface of a liquid or solid active agent, adsorbed to a liquid droplet of an emulsion comprising dissolved or suspended active active agent, adsorbed to a solid active agent within a liquid droplet of an emulsion, or a combination thereof, exhibit exceptional bioadhesion to biological surfaces, such as hair, mucous, skin, plant tissue, etc. The active agent can be either soluble or insoluble. In addition, the active agent can be either crystalline, semi-crystalline, amorphous, in a liquid state at or near room temperature, or a combination thereof.

The active agent particles of the nanoparticulate composition, when in either a solid or a liquid state, have an effective average particle size of less than about 4000 nm. If the active agent is dissolved or dispersed in a liquid droplet of an emulsion, then the liquid droplet has an effective average particle size of less than about 4000 nm. The active agent particle, or liquid droplet of an emulsion comprising active agent, can also have an effective average particle size of less than about less than about 3500 nm, less than about 3000 nm, less than about 2500 nm, less than about 2000 nm, less than about 1500 nm, less than about 1000 nm, less than about 800 nm, less than about 700 nm, less than about 600 nm, less than about 500 nm, less than about 400 nm, less than about 300 nm, less than about 250 nm, less than about 200 nm, less than about 100 nm, and less than about 50 nm. The active agent particles can be dispersed in a liquid medium or used in dry form.

In a first embodiment, the active agent is a poorly water-soluble compound in a crystalline, semi-crystalline, an amorphous state, or a combination thereof. The stable bioadhesive nanoparticulate composition comprises the poorly water-soluble active agent and, adsorbed to the surface of the agent, at least one cationic surface stabilizer.

In a second embodiment, the active agent is a poorly water-soluble compound which is in a liquid state at or near room temperature. The stable bioadhesive nanoparticulate composition comprises the liquid poorly water-soluble active agent and, adsorbed to the droplet surface of the liquid agent, at least one cationic surface stabilizer. The liquid active agent droplets are dispersed in a liquid medium in which they are poorly soluble, such as water.

In a third embodiment, the active agent is a water-soluble compound in a crystalline, semi-crystalline, an amorphous state, or a combination thereof. The stable bioadhesive nanoparticulate composition comprises the water-soluble active agent and, adsorbed to the surface of the agent, at least one cationic surface stabilizer.

In a fourth embodiment, the active agent is a water-soluble compound which is in a liquid state at or near room temperature. The stable bioadhesive nanoparticulate composition comprises the liquid water-soluble active agent and, adsorbed to the droplet surface of the liquid agent, at least one cationic surface stabilizer. The active agent liquid droplets are dispersed in a liquid medium in which they are poorly soluble, such as mineral oil, ethanol, vegetable oils (corn, safflower, olive, etc.), or a hydrocarbon.

In a fifth embodiment, the active agent particles are dissolved or dispersed in liquid droplets of a poorly water-soluble liquid, such as mineral oil, vegetable oils (corn, safflower, olive, etc.), or a hydrocarbon. At least one cationic surface stabilizer is adsorbed to the surface of the liquid droplets. For this composition, the liquid droplets comprising active agent are dispersed in a liquid medium in which they are poorly soluble, such as water. In addition, the liquid droplets comprising active agent have an effective average particle size of less than about 4000 nm. In a variation of this composition, active agent particles dispersed in the liquid droplets have at least one cationic surface stabilizer adsorbed to the surface of the active agent, and at least one cationic surface stabilizer is also adsorbed to the surface of the liquid droplet comprising the active agent. The two cationic surface stabilizers can be the same or different. The liquid droplets comprising the active agent have an effective average particle size of less than about 4000 nm.

In a sixth embodiment, active agent particles are dissolved or dispersed in liquid droplets of a water-soluble liquid, such as water. At least one cationic surface stabilizer is adsorbed to the surface of the liquid droplets. For this composition, the liquid droplets comprising active agent are dispersed in a liquid medium in which they are poorly soluble, such as mineral oil, vegetable oils (corn, safflower, olive, etc.), or a hydrocarbon. In addition, the liquid droplets comprising active agent have an effective average particle size of less than about 4000 nm.

Another aspect of the invention is directed to pharmaceutical compositions comprising one or more nanoparticulate compositions of the invention. The pharmaceutical composition preferably comprises a nanoparticulate composition described above and a pharmaceutically acceptable carrier, as well as any desired excipients.

A. Summary of Bioadhesion

The term bioadhesion refers to any attractive interaction between two biological surfaces or between a biological and a synthetic surface. In the case of bioadhesive nanoparticulate compositions, the term bioadhesion is used to describe the adhesion between the nanoparticulate compositions and a biological substrate (i.e. gastrointestinal mucin). There are basically two mechanisms which may be responsible for this bioadhesion phenomena. These are mechanical or physical interactions and chemical interactions. The first of these, mechanical or physical mechanisms, involves the physical interlocking or interpenetration between a bioadhesive entity and the receptor tissue, resulting from a good wetting of the bioadhesive surface, swelling of the bioadhesive polymer, penetration of the bioadhesive entity into a crevice of the tissue surface, or interpenetration of bioadhesive composition chains with those of the mucous or other such related tissues. The second possible mechanism of bioadhesion, chemical, incorporates strong primary bonds (i.e., covalent bonds) as well as weaker secondary forces such as ionic attraction, van der Waals interactions and hydrogen bonds. It is this chemical form of bioadhesion which is primarily responsible for the bioadhesive properties of the nanoparticles described in this patent. However, physical and mechanical interactions may also play a secondary role in the bioadhesion of such nanoparticles.

Because of the character of biological surfaces, the cationic surface stabilizers of the invention result in bioadhesive formulations. Surprisingly, the bioadhesive property of cationic particles diminishes as the particle size of the active agent increases, as noted in more detail below.

B. Applications of the Nanoparticulate Compositions of the Invention

The bioadhesive nanoparticulate compositions are useful in any situation in which it is desirable to apply an active agent to a biological surface. For example, the bioadhesive nanoparticulate compositions of the invention can be used in pharmaceuticals, including biologics such as proteins and peptides, organic compounds, such as therapeutic small molecules, agricultural agents, cosmetic agents, hair compositions, and others. The bioadhesive nanoparticulate compositions of the invention coat the targeted surface in a continuous and uniform film which is invisible to the naked human eye.

The bioadhesive compositions can be applied to any plant or animal surface. For example, insects or pests can be treated with insecticides, plants can be treated with herbicides, etc.

The adhesion exhibited by the inventive compositions means that the active agent nanoparticles are not easily washed off, rubbed off, or otherwise removed from the biological surface for an extended period of time. The period of time in which a biological cell surface is replaced is the factor that limits retention of the bioadhesive nanoparticles to that biological surface. For example, skin cells are replaced every 24–48 hours. Thus, the nanoparticulate composition would have to be reapplied to the skin every 48 hours. Mucous cells shed and are replaced about every 5–6 hours. Other biological surfaces, such as chitin, hair, teeth, and bone, do not routinely shed cells and, therefore, repeat applications may not be necessary.

C. Nanoparticulate Compositions

1. Active Agents

The nanoparticles of the invention comprise an active agent. The active agent exists in a crystalline phase, semi-crystalline phase, in an amorphous phase, in a liquid state at or near room temperature, or a combination thereof. The crystalline phase differs from a non-crystalline or amorphous phase can which result from precipitation techniques, such as those described in EP Patent No. 275,796. If the agent is poorly soluble, it is preferably dispersible in at least one liquid medium. By "poorly soluble" it is meant that the agent has a solubility in the liquid dispersion medium of less than about 10 mg/mL, and preferably of less than about 1 mg/mL. By "soluble," it is meant that the active agent has a solubility in the liquid dispersion medium of greater than about 10 mg/mL.

The active agent can be a drug, which is preferably present in an essentially pure form. A drug can be selected from a variety of known classes of drugs, as provided in U.S. Pat. No. 5,145,684, including, for example, proteins, peptides, nutriceuticals, anti-obesity agents, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, cough suppressants (expectorants and mucolytics), diagnostic agents, diagnostic imaging agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines.

Drugs to be administered in an aerosol formulation are preferably selected from the group consisting of proteins, peptide, bronchodilators, corticosteroids, elastase inhibitors, analgesics, anti-fungals, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, fungal infection therapies, respiratory illness therapies associated with acquired immune deficiency syndrome, an oncology drug, an anti-emetic, an analgesic, and a cardiovascular agent.

A description of these classes of drugs and a listing of species within each class can be found in Martindale, *The Extra Pharmacopoeia*, Twenty-ninth Edition (The Pharmaceutical Press, London, 1989), specifically incorporated by reference. The drugs are commercially available and/or can be prepared by techniques known in the art.

a. Active Agents Useful in Dermal Applications

The active agents according to the present invention include but are not limited to active agents which can be used in dermal applications, e.g., sunscreens, cosmetics, topical application of pharmaceuticals to the dermis (acne medication, anti-wrinkle drugs, such as alpha-hydroxy formulations), nail polish, moisturizers, deodorant, etc.

Cosmetic compositions are generally defined as compositions suitable for application to the human body. Cosmetic compositions such as creams and lotions are used to moisturize the skin and keep it in a smooth, supple condition. Pigmented cosmetic compositions, such as makeup, blush, lipstick, and eye shadow, are used to color the skin and lips. Since color is one of the most important reasons for wearing cosmetics, color-containing cosmetics must be carefully formulated to provide maximum wear and effect.

One of the long standing problems with pigmented cosmetic compositions, such as face makeup, lipstick, mascara, and the like, is the tendency of the cosmetic to blot or transfer from the skin or lashes onto other surfaces, such as glassware, silverware, or clothing. This blotting not only creates soiling but it also forces the cosmetic user to reapply cosmetic at fairly short intervals.

Traditional pigmented cosmetic compositions are either water and oil emulsions containing pigments, or they are anhydrous systems containing waxes, oils, and pigments. These formulations are applied and blended into the skin to provide color and to correct skin topography to provide an even, smooth appearance. The films are simply deposited on the surface of the skin and if touched with fingers the product may transfer or become blotchy and uneven. Perspiration or sebum will break through the film and cause running or smearing. If skin comes into contact with clothing, the clothing may become soiled.

Other areas which benefit from the present invention include coloring agents, flavors and fragrances. Coloring agents or pigments are used in cosmetic applications as well as in fabric applications. Suitable pigments can be inorganic and/or organic. Also included within the term pigment are materials having a low color or luster, such as matte finishing agents, and also light scattering agents. Examples of suitable pigments are iron oxides, acylglutamate iron oxides, ultramarine blue, D&C dyes, carmine, and mixtures thereof. Depending upon the type of cosmetic composition, e.g., foundation or blusher, a mixture of pigments will normally be used.

Bioadhesive nanoparticulate cosmetic compositions satisfy a long-felt need for cosmetic compositions that strongly adhere to the biological surface to which they are applied.

Fragrances and odiferous compounds are also suitable for use in the present inventive compositions. Fragrances or perfumes are usually prepared from volatile oils distilled or extracted from the leaves, flowers, gums, or woods of plant life (occasionally from animal life). These include, for example, linalyl acetate from citral, jasmine, cedar, lavender, and attar of rose. A typical fragrance may consist of many volatile components blended to create a pleasant sensory experience to the person wearing the fragrance and also impart a pleasant sensory experience to the people around that person. These blended oils, however, are typically too potent or too expensive to wear without being diluted in an appropriate solvent. Present perfumeries use lower molecular weight alcohol, e.g., methanol or ethanol, and more typically ethanol, to prepare a variety of "perfume" products, such as eau de cologne, perfume, eau de parfum, eau de toilette, splash cologne, and eau fraiche for the consumer. Bioadhesive nanoparticulate compositions comprising a fragrance or odiferous compound as an active agent could provide prolonged sensory stimulation following application; i.e., for up to 48 hours following application to the skin.

b. Active Agents Useful in Mucous Applications

Exemplary active agents to be applied to mucous include dental applications, such as oral bioadhesive nanoparticulate lidocain formulations, bioadhesive nanoparticulate fluoride treatments, application to the lungs, throat, GIT, application to wounds, etc.

Also included is application to the throat using a liquid containing a bioadhesive nanoparticulate formulation containing, for example, menthol or other numbing compound for treatment of coughs or sore throats. The stomach and GIT can also be treated using bioadhesive formulations. This is particularly useful for treatment of diseases associated with the mucous of the gastrointestinal tract, such as Crohn's Disease.

Other pharmaceutical therapeutic methodologies include oral dosing, nasal administration, vaginal administration, ocular administration, colonic, and subcutaneous administration.

The compositions of the invention also encompass food products. For example, spice, oleoresin, flavor oil, color, or chemicals are often added during food processing to produce the desirable flavors, taste, and appearance. These agents can be included in a bioadhesive nanoparticulate composition of the present invention for increased adhesion to biological surfaces. Bioadhesive nanoparticulate flavoring agents could be used in products such as gums to produce prolonged flavor.

c. Active Agents Useful in Hair Applications

Biological substrates such as the hair are also encompassed by the scope of the invention. Bioadhesive nanoparticulate compositions can be used in hair conditioner formulations, hair dyes, hair sprays, hair cosmetics, hair cleansers, depilatories, etc.

d. Active Agents Useful in Plant Tissue Applications

Yet another area of applicability of the present invention includes bioadhesive nanoparticulate compositions that can be applied to plant tissue. Because of the difficulty in solubilizing some agricultural agents (i.e., some agricultural agents are applied as insoluble powders), the present invention provides a superior application method for plants as compared to prior art plant application methods.

Bioadhesive nanoparticulate compositions can be used for applications of pesticides, insecticides, fertilizers, etc.—any substance to be applied to the surface of a plant. All plants, such as grass, trees, commercial farm crops (such as corn, soybeans, cotton, vegetables, fruit, etc), weeds, etc., are encompassed by the scope of this invention.

In one embodiment of the invention, the active agent of the bioadhesive nanoparticulate composition is an insecticidal ingredient applied to seeds, plants, trees, harvested crops, soil, and the like. The insecticide ingredient can be selected from a wide variety of organic compounds or mixtures which are known and used in agriculture and horticulture applications, such as those listed in W. T. Thomson, *Agricultural Chemicals, Book I, Insecticides* (Thomson Publications, Fresno, Calif. 1989).

The general categories of insecticidal-active organic compounds include chlorinated hydrocarbon derivatives, phosphorated derivatives, pyrethroids, acylureas, and the like. Chlorinated hydrocarbon insecticides usually act as stomach and contact poisons affecting the nervous system. They are persistent in the environment and tend to accumulate in animal fatty tissue, as exemplified by DDT and chlordane.

Illustrative of other insecticidal compounds are chlorfluazuron, chlorpyrifos, chlorpyrifos methyl, bromophos, diazinon, malathion, trichlorfon, dimethoate, phorate, lindane, toxaphene, diflubenuron, methomyl, propoxur, carbaryl, cyhexatin, cypermethrin, permethrin, fenvalerate, dicofol, tetradifon, propargite, and the like. Other examples of insecticides include the pyrethroid insecticides, such a Fenvalerate™ [α-cyano-3-phenoxybenzyl-2-(4-chlorophenyl)-3methylvalerate] and Pyrethroid™ [cyano(4-fluoro-3-phenoxyphenylmethyl-3-(2,2-dichloroethenyl)-2,2-dimethyl cyclopropanecarboxylate]; organophosphorus insecticides, such as DDVP™ (2,2-dichlorovinyldimethyl phosphate), Sumithion™ (dimethyl-4-nitro-m-tolylphosphorothionate), Malathone™ {S-[1,2-bis(ethoxycarbonyl)ethyl]dimethylphosphorothiol thionate}, Dimethoate [dimethyl-S-(N-methylcarbamoylmethyl)-phosphorothios thionate), Elsan™ {S-[.alpha.-(ethoxycarbonyl)benzyl] dimethylphosphorothiol thionate), and Baycid™ [O,O-dimethyl-O-(3-methyl-4methylmercaptophenyl) thiophosphate]; carbamate; insecticides such as Bassa™ (O-butylphenyl methylcarbamate), MTMC™ (m-tolyl methylcarbamate), Meobal™ (3,4-dimethylphenyl-N-methylcarbamate), and NAC™ (1-naphthyl-N-methylcarbamate); as well as Methomyl™ {methyl-N [(methylcarbamoyl)oxy]thioacetimide} and Cartap™ {1,3-bis(carbamolythio)-2-(N,N-dimethylamino)propane hydrochloride}.

Examples of other agricultural agents include acaricides such as, but not limited to, Smite™ {2-[2-(p-tert-butylphenoxy)isopropoxy]isopropyl-2-chloroethyl sulfide}, Acricid™ (2,4-dinitro-6-sec-butylphenyl dimethylacrylate), Chlormit™ (isopropyl 4,4-dichlorobenzylate), Acar™ (ethyl 4,4-dichlorobenzylate), Kelthane™ [1,1-bis(p-chlorophenyl)-2,2,2-trichloroethanol], Citrazon™ (ethyl O-benzoyl-3-chloro-2,6-dimethoxybenzohydroxymate), Plictran™ (tricyclohexyltin hydroxide), and Omite™ [2-(p-tert-butylphenoxy)cyclohexyl-2-propinyl sulfite].

Examples of germicides include organosulfur germicides, such as Dithane™ (zinc ethylenebisdithiocarbamate), Maneo™ (manganese ethylenebis-dithiocarbamate), Thiuram™ [bis(dimethylthiocarbamoyl) disulfide ], Benlate™ [methyl 1-(butylcarbamoyl)-2-benzimidazole carbamate], Difolatan (N-tetrachloroethylthio-4-cyclohexane-1,2-dicarboxyimide), Daconol™ (tetrachloroisophthalonitrile), Pansoil™ (5-ethoxy-3-trichloromethyl-1,2,4-thiadiazole), Thiophanate-methyl[1,2-bis(3-methoxycarbonyl-2-thioureido)benzene], Rabcide™ (4,5,6,7-tetrachlorophthaloid), Kitazin P™ (O, O-diisopropyl-S-benzyl phosphorothioate), Hinonsan™ (O-ethyl-S,S-diphenyldithiophosphate), and Propenazol™ (3-allyloxy-1, 2-benzothiazole 1,1-dioxide).

Example of plant growth regulating agents include, but are not limited to, MH™ (maleic acid hydrazide) and Ethrel™ (2-chloroethylphosphonic acid).

Examples of herbicides include, but are not limited to Stam™ (3,4-dichloropropionanilide), Saturn™ [S-(4-chlorobenzyl) N,N-diethylthiolcarbamate), Lasso (2-chloro-2',6'-diethylN-(methoxymethyl)acetanilide), Glyphosate™ [N-(phosphonomethyl)glycine isopropylamine salt], DCMU [3-(3,4-dichlorophenyl)-1,1-dimethylurea), and Gramoxone™ (1,1'-dimethyl-4,4'-dipyridium dichloride].

Other herbicides contemplated for use in the present invention include auxin transport inhibitors, e.g., naptalam; growth regulators, including benzoic acids, e.g., dicamba; phenoxy acids, such as (i) acetic acid type, e.g., 2,4-D, MCPA, (ii) propionic acid type, e.g., 2,4-DP, MCPP, and (iii) butyric acid type, e.g., 2,4-DB, MCPB; picolinic acids and related compounds, e.g., picloram, triclopyr, fluroxypyr, and clopyralid.

Photosynthesis inhibitors are also herbicides useful in the compositions of the invention. Such compounds include but are not limited to (a) s-triazines, such as (i) chloro substituted, e.g., atrazine, simazine, and cyanazine, (ii) methoxy substituted, e.g., prometon, (iii) methylthio substituted, e.g., ametryn and prometryn; (b) other triazines, such as hexazinone, and metribuzin; (c) substituted ureas, such as diuron, fluometuron, linuron, tebuthiuron, thidiazuron, and forchlorfenuron; (d) uracils, such as bromacil and terbacil; and (e) others, such as bentazon, desmedipham, pheninedipham, propanil, pyrazon, and pyridate.

Pigment inhibitors are also herbicides useful in the compositions of the invention. Such compounds include but are not limited to pyridazinones, such as norflurazon; isoxazolones, such as clomazone; and others, such as amitrole and fluridone.

In yet another aspect of the invention, growth inhibitors are herbicides useful in the compositions of the invention. Such compounds include but are not limited to (a) mitotic disruptors, such as (i) dinitroanilines, e.g., trifluralin, prodiamine, benefin, ethalfluralin, isopropalin, oryzalin, and pendimethalin; and (ii) others, such as DCPA, dithiopyr, thiazopyr, and pronamide; (b) inhibitors of shoots of emerging seedlings, such as (i) thiocarbamates, e.g., EPTC, butylate, cycloate, molinate, pebulate, thiobencarb, triallate, and vernolate; (c) inhibitors of roots only of seedlings, such as bensulide, napropamide, and siduron; and (d) inhibitors of roots and shoots of seedlings, including chloroacetamides, such as alachlor, acetochlor, metolachlor, diethatyl, propachlor, butachlor, pretilachlor, metazachlor, dimethachlor, and cinmethylin.

Amino acid synthesis inhibitors are herbicides useful in the compositions of the invention. Such compounds include, but are not limited to, (a) glyphosate, glufosinate; (b) sulfonylureas, such as rimsulfuron, metsulfuron, nicosulfuron, triasulfuron, primisulfuron, bensulfuron, chlorimuron, chlorsulfuron, sulfometuron, thifensulfuron, tribenuron, ethametsulfuron, triflusulfuron, clopyrasulfuron, pyrazasulfuron, prosulfuron (CGA-152005), halosulfuron, metsulfuron-methyl, and chlorimuron-ethyl; (c) sulfonamides, such as flumetsulam (a.k.a. DE498); (d) imidazolinones, such as imazaquin, imazamethabenz, imazapyr, imazethapyr, and imazmethapyr.

Lipid biosynthesis inhibitors are herbicides useful in the compositions of the invention. Such compounds include, but are not limited to, (a) cyclohexanediones, such as sethoxydim and clethodim; (b) aryloxyphenoxys, such as fluazifop-(P-butyl), diclofop-methyl, haloxyfop-methyl, and quizalofop; and (c) others, such as fenoxaprop-ethyl.

Cell wall biosynthesis inhibitors are herbicides useful in the compositions of the invention. Such compounds include, but are not limited to, dichlobenil and isoxaben.

Rapid cell membrane disruptors are herbicides useful in the compositions of the invention. Such compounds include, but are not limited to, (a) bipyridiliums, such as paraquat, and diquat; (b) diphenyl ethers, such as acifluorfen, fomesafen, lactofen, and oxyfluorfen; (c) glutamine synthetase inhibitors, such as glufosinate; and (d) others, such as oxadiazon.

Miscellaneous herbicides useful in the compositions of the invention include, but are not limited to, (a) carbamates, such as asulam; (b) nitriles, such as bromoxynil and ioxynil; (c) hydantocidin and derivatives; and (d) various other compounds, such as paclobutrazol, ethofumesate, quinclorac (a.k.a. BAS514), difenzoquat. endothall, fosamine, DSMA, and MSMA.

Other herbicides useful in the compositions of the invention include, but are not limited to, triketones and diones of the type described in U.S. Pat. Nos. 5,336,662 and 5,608,101, the contents of each of which are incorporated herein by reference, and in EP-A-338-992; EP-A-394-889; EP-A-506,967; EP-A-137,963; EP-A-186-118; EP-A-186-119; EP-A-186-120; EP-A-249-150; and EP-A-336-898. Examples of such triketones and diones are sulcotrione (MIKADO™), whose chemical designation is 2-(2-chloro-4-methanesulfonylbenzoyl)-1,3-cyclohexanedione: 2-(4-methylsulfonyloxy-2-nitrobenzoyl)-4,4,6,6-tetramethyl-1,3-cyclohexane dione; 3-(4-methylsulfonyloxy-2-nitrobenzoyl)-bicyclo[3,2,1]octane-2,4-dione3-(4-methylsulfonyl-2-nitrobenzoyl)-bicyclo[3,2,1]octane-2,4-dione; 4-(4-chloro-2-nitrobenzoyl)-2,6,6-trimethyl-2H-1,2-oxazine-3,5(4H,6H)dione; 4-(4-methylthio-2-nitrobenzoyl)-2,6,6-trimethyl-2H-1,2-oxazine-3,5( 4H,6H) -dione; 3-(4-methylthio-2-nitrobenzoyl)-bicyclo[3,2,1]octane-2,4-dione; 4-(2-nitro-4-trifluoromethoxybenzoyl)-2,6,6-trimethyl-2H-1,2-oxazine-3,5(4 H,6H)-dione.

Herbicidal compounds useful in the nanoparticulate compositions of the invention are described in U.S. Pat. No. 5,506,192; EP-A-461,079; EP-A-549,524; EP-A-315,589 and PCT Appln. No. 91/10653. The contents of all of the cited references are incorporated herein by reference; including for example 3-[(4,6-dimethoxy-2-pyrimidinyl) hydroxymethyl]-N-methyl-2-pyridine carboxamide; 4,7-dichloro-3-(4,6-dimethoxy-2-pyrimidinyl)-3-hexanoyloxyphthalide; 3-[(4,6-dimethoxy-2-pyrimidinyl) carbonyl]-N,N-dimethyl-2-pyridine carboxamide; 3,6-dichloro-2-[(4,6-dimethoxy-2-pyrimidinyl)carbonyl] benzoic acid; 6-chloro-2-[(4,6-dimethoxy-2-pyrimidinyl) thio]benzoic acid (a.k.a. DPX-PE350 or pyrithiobac) and salts thereof.

e. Agents Useful in Miscellaneous Applications

Other exemplary uses of the novel bioadhesive formulations are provided: teeth can be treated with teeth whiteners or fluoride bioadhesive compositions; bones can be treated with calcium bioadhesive compositions; nails can be treated with color or strengthening bioadhesive formulations; insects or pests can be treated with insecticides or other toxic compositions to the pest. In sum, the compositions are useful in treating any biological surface, or a surface derived from a biological material. Feathers and scales of animals can be treated, as well as other animal biological surfaces such as chitin.

2. Surface Stabilizers

Surface stabilizers useful herein physically adhere to the surface of the nanoparticulate active agent, or liquid emulsion droplet comprising the active agent, but do not chemically react with the active agent or itself. Individually adsorbed molecules of the surface stabilizer are essentially free of intermolecular crosslinkages. The surface stabilizers are commercially available and/or can be prepared by techniques known in the art. Examples of useful cationic surface stabilizers include but are not limited to polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammoniumbromide bromide (PMMTMABr), hexyldesyltrimethylammonium bromide (HDMAB), and polyvinylpyrrolidone-2-dimethylaminoethyl methacrylate dimethyl sulfate.

Other useful cationic stabilizers include, but are not limited to, cationic lipids, sulfonium, phosphonium, and quarternary ammonium compounds, such as stearyltrimethylammonium chloride, benzyl-di(2-chloroethyl) ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl ($C_{12-18}$)dimethylbenzyl ammonium chloride, N-alkyl ($C_{14-18}$)dimethyl-benzyl ammonium chloride, N-tetradecylidmethylbenzyl ammonium chloride monohydrate, dimethyl didecyl ammonium chloride, N-alkyl and ($C_{12-14}$) dimethyl 1-napthylmethyl ammonium chloride, trimethylammonium halide, alkyl-trimethylammonium salts and dialkyl-dimethylammonium salts, lauryl trimethyl ammonium chloride, ethoxylated alkyamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$) dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, $C_{17}$ trimethyl ammonium bromides, dodecylbenzyl triethyl ammonium chloride, polydiallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUA™ (Alkaril Chemical Company), alkyl pyridinium salts; amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides; imide azolinium salts; protonated quaternary acrylamides; methylated quaternary polymers, such as poly[diallyl dimethylammonium chloride] and poly-[N-methyl vinyl pyridinium chloride]; and cationic guar.

Such exemplary cationic surface stabilizers and other useful cationic surface stabilizers are described in J. Cross and E. Singer, *Cationic Surfactants: Analytical and Biological Evaluation* (Marcel Dekker, 1994); P. and D. Rubingh (Editor), *Cationic Surfactants: Physical Chemistry* (Marcel Dekker, 1991); and J. Richmond, *Cationic Surfactants: Organic Chemistry*, (Marcel Dekker, 1990).

Particularly preferred nonpolymeric primary stabilizers for crystalline active agents are any nonpolymeric compound other than benzalkonium chloride. Such compounds can be a carbonium compound, a phosphonium compound, an oxonium compound, a halonium compound, a cationic organometallic compound, a quarternary phosphorous compound, a pyridinium compound, an anilinium compound, an immonium compound, a hydroxylammonium compound, a primary ammonium compound, a secondary ammonium compound, a tertiary ammonium compound, and quarternary ammonium compounds of the formula $NR_1R_2R_3R_4^{(+)}$. For compounds of the formula $NR_1R_2R_3R_4^{(+)}$:

(i) none of $R_1$–$R_4$ are $CH_3$;
(ii) one of $R_1$–$R_4$ is $CH_3$;
(iii) three of $R_1$–$R_4$ are $CH_3$;
(iv) all of $R_1$–$R_4$ are $CH_3$;
(v) two of $R_1$–$R_4$ are $CH_3$, one of $R_1$–$R_4$ is $C_6H_5CH_2$, and one of $R_1$–$R_4$ is an alkyl chain of seven carbon atoms or less;
(vi) two of $R_1$–$R_4$ are $CH_3$, one of $R_1$–$R_4$ is $C_6H_5CH_2$, and one of $R_1$–$R_4$ is an alkyl chain of nineteen carbon atoms or more;
(vii) two of $R_1$–$R_4$ are $CH_3$ and one of $R_1$–$R_4$ is the group $C_6H_5(CH_2)_n$, where n>1;
(viii) two of $R_1$–$R_4$ are $CH_3$, one of $R_1$–$R_4$ is $C_6H_5CH_2$, and one of $R_1$–$R_4$ comprises at least one heteroatom;
(ix) two of $R_1$–$R_4$ are $CH_3$, one of $R_1$–$R_4$ is $C_6H_5CH_2$, and one of $R_1$–$R_4$ comprises at least one halogen;
(x) two of $R_1$–$R_4$ are $CH_3$, one of $R_1$–$R_4$ is $C_6H_5CH_2$, and one of $R_1$–$R_4$ comprises at least one cyclic fragment;
(xi) two of $R_1$–$R_4$ are $CH_3$ and one of $R_1$–$R_4$ is a phenyl ring; or
(xii) two of $R_1$–$R_4$ are $CH_3$ and two of $R_1$–$R_4$ are purely aliphatic fragments.

Such compounds include, but are not limited to, behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride(Quaternium-14), Quaternium-22, Quaternium-26, Quatenium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride,7 myrtrimonium bromide, oleyltrimonium chloride, polyquaternium-1, procainehydrochloride, cocobetaine, stearalkonium bentonite, stearalkoniumhectorite, stearyl trihydroxyethyl propylenediamine dihydrofluoride, tallowtrimonium chloride, and hexadecyltrimethyl ammonium bromide. All of these nonpolymeric surface stabilizers can be used with semi-crystalline and amorphous active agents, as well as crystalline active agents.

All of these stabilizers can be used for amorphous, semi-crystalline, or any combination of amorphous, semi-crystalline, and crystalline active agents.

Secondary non-cationic surface stabilizers can also be added to the compositions of the invention. Benzalkonium chloride (BKC) is useful as a secondary stabilizer for crystalline compounds. BKC is useful as a primary stabilizer for amorphous, semi-crystalline, or mixtures of amorphous, semi-crystalline, and/or crystalline compositions.

3. Nanoparticulate Active Agent/Surface Stabilizer Particle Size

The compositions of the invention contain active agent nanoparticles which have an effective average particle size of less than about 4 microns, less than about 3.5 microns, less than about 3 microns, less than about 2.5 microns, less than about 2 microns, less than about 1.5 microns, less than about 1 micron, less than about 800 nm, less than about 700 nm, less than about 600 nm, less than about 500 nm, less than about 400 nm, less than about 300 nm, less than about 200 nm, less than about 100 nm, or less than about 50 nm, as measured by light-scattering methods, microscopy, or other appropriate methods.

If the active agent is dissolved or dispersed in a liquid droplet of an emulsion, then the liquid droplet comprising the active agent has a particle size of less than about 4 microns, less than about 3.5 microns, less than about 3 microns, less than about 2.5 microns, less than about 2 microns, less than about 1.5 microns, less than about 1 micron, less than about 800 nm, less than about 700 nm, less than about 600 nm, less than about 500 nm, less than about 400 nm, less than about 300 nm, less than about 200 run, less than about 100 nm, or less than about 50 nm, as measured by light-scattering methods, microscopy, or other appropriate methods.

By "an effective average particle size of "less than about 4 microns," it is meant that at least 50% of the active agent particles, or liquid droplets comprising active agent, have a weight average particle size of less than about 4 microns when measured by light scattering techniques, microscopy, or other appropriate methods. Preferably, at least 70% of the active agent particles, or liquid droplets containing active agent, have an average particle size of less than about 4 microns, more preferably at least 90% of the active agent particles, or liquid droplets containing active agent, have an average particle size of less than about 4 microns, and even more preferably at least about 95% of the particles or liquid droplets have a weight average particle size of less than about 4 microns.

It was unexpectedly discovered that the bioadhesive property of the nanoparticulate compositions of the invention is dependent upon the particle size of the active agent, or liquid droplets comprising active agent, present in the nanoparticulate composition. Optimal bioadhesive characteristics are observed with the effective average particle size of the active agent present in the nanoparticulate composition or liquid droplets comprising active agent, is less than about 1 micron. However, the bioadhesive property is still present, but minimal, up to about 6 microns. Larger particles do not exhibit strong bioadhesive properties. This is demonstrated by the results given in the examples in which large micron-sized drugs combined with cationic stabilizers did not exhibit bioadhesive properties.

4. Concentration of Nanoparticulate Active Agent and Surface Stabilizer

The relative amount of active agent and one or more surface stabilizers can vary widely. The optimal amount of the one or more surface stabilizers can depend, for example, upon the particular active agent selected, the hydrophilic lipophilic balance (HLB), melting point, and water solubility of the surface stabilizer, and the surface tension of water solutions of the surface stabilizer, etc.

The amount of stabilizer present is from about 0.001 to about 99.999% w/v, preferably from about 0.25 to about 25% w/v, more preferably from about 0.5 to about 15% w/v, and most preferably from about 1 to about 10% w/v, based on the total weight of the composition.

The concentration of the active agent can vary from about 99.99% to about 0.01% w/v, preferably from about 90% to about 0.1% w/v, more preferably from about 70% to about 1% w/v, more preferably from about 60% to about 2% w/v, and most preferably from about 50% to about 5% w/v, by weight based on the total weight of the composition.

D. Methods of Making Nanoparticulate Compositions

This invention further discloses methods of making nanoparticulate compositions according to the invention. A first method comprises contacting a nanoparticulate active agent with at least one cationic surface stabilizer for a time and under conditions sufficient to provide a stable nanoparticulate composition in which the cationic surface stabilizer is adsorbed to the surface of the active agent particles. The cationic surface stabilizer can be contacted with the active agent either before, during, or after size reduction of the active agent. The agent can be either crystalline, semi-crystalline, or amorphous. The active agent particles of the nanoparticulate composition have an effective average particle size of less than about 4 microns, less than about 3.5 microns, less than about 3 microns, less than about 2.5 microns, less than about 2 microns, less than about 1.5 microns, less than about 1 micron, less than about 800 nm, less than about 700 nm, less than about 600 nm, less than about 500 nm, less than about 400 nm, less than about 300 nm, less than about 200 nm, less than about 100 nm, or less than about 50 nm. The effective average particle size can be achieved by wet milling techniques, by controlled precipitation methods, or by other suitable size reduction methods, such as by homogenization. Exemplary milling, precipitation, and homogenization methods of making nanoparticulate compositions are described in U.S. Pat. Nos. 5,145,684; 5,518,187; 5,718,388; 5,862,999; 5,510,118; and 5,766,635.

Microprecipitation is a method of preparing stable dispersions of the active agents in the presence of one or more surface stabilizers free of any trace toxic solvents or solubilized heavy metal impurities. Such a method comprises, for example: (1) dissolving the active agent in a suitable solvent; (2) adding the formulation from step (1) to a solution comprising at least one cationic surface stabilizer to form a clear solution; and (3) precipitating the formulation from step (2) using an appropriate non-solvent. The method can be followed by removal of any formed salt, if present, by dialysis or diafiltration and concentration of the dispersion by conventional means. The resultant nanoparticulate dispersion can be utilized in solid or liquid formulations.

In cases where the active agent is a liquid at or near room temperature, or where the active agent is dissolved or dispersed in either a water-soluble or water-insoluble liquid, the nanoparticulate composition is in the form of an emulsion. In such cases, a method of making the emulsion comprises combining the active agent with an emulsifying agent and a liquid non-solvent and processing the resultant mixture with a homogenizer, high-shear mixer, rotor-stator type device, Microfluidizer®, or other such equipment which is suitable for preparing emulsions and is well known to those skilled in the art.

If the active agent is present as droplets within an emulsion, then the active agent nanoparticles also comprise at least one cationic surface stabilizer adsorbed to the surface of the liquid active agent particles. If the active agent is solubilized in the liquid droplets of the emulsion, then the liquid droplets comprising the active agent have at least one cationic surface stabilizer adsorbed to the surface of the liquid droplets. If the active agent is insoluble in the liquid droplets of the emulsion, then the active agent nanoparticles comprise at least one cationic surface stabilizer adsorbed to the surface of the particles, the liquid droplets comprising the active agent comprise at least one cationic surface stabilizer adsorbed to the surface of the liquid droplets, or the particulate active agent in the liquid droplets and the liquid droplets comprise at least one cationic surface stabilizer adsorbed to the surface of the active agent particles and liquid emulsion droplets. The cationic surface modifiers may be present during the emulsification process or may be added after the emulsion has been formed. Exemplary microfluidization methods for making nanoparticulate compositions are described in U.S. Pat. No. 5,510,118.

If the active agent is a liquid at or near room temperature, or if the active agent particles are solubilized or dispersed in the liquid droplets of the emulsion, then the liquid droplets of the emulsion comprising the active agent (in either a pure, solubilized, or particulate state) have an effective average particle size of less than about 4 microns, less than about 3.5 microns, less than about 3 microns, less than about 2.5 microns, less than about 2 microns, less than about 1.5 microns, less than about 1 micron, less than about 800 nm, less than about 700 nm, less than about 600 nm, less than about 500 nm, less than about 400 nm, less than about 300 nm, less than about 200 nm, less than about 100 nm, or less than about 50 nm.

In a third method, aqueous nanoparticulate dispersions of water-soluble active agents can be prepared by encapsulating the active agent particles with a suitable coating and then dispersing them in water. The water-soluble nanoparticles can be prepared by wet milling in liquid nonsolvents, controlled precipitation, or other methods known to those in the art. After removal of the nonsolvents by evaporation, the nanoparticles can be treated with a protective coating, such as ethylcellulose, and subsequently dispersed in an aqueous vehicle. At least one cationic surface modifier is adsorbed to the surface of the encapsulated nanoparticles. The encapsulated nanoparticles have an effective average particle size of less than about 4 microns, less than about 3.5 microns, less than about 3 microns, less than about 2.5 microns, less than about 2 microns, less than about 1.5 microns, less than about 1 micron, less than about 800 nm, less than about 700 nm, less than about 600 nm, less than about 500 nm, less than about 400 nm, less than about 300 nm, less than about 200 nm, less than about 100 nm, or less than about 50 nm.

E. Methods of Using the Nanoparticulate Compositions

The nanoparticulate compositions of the present invention can be administered to biological surfaces, such as mucous and skin, of humans and animals either orally, rectally, parenterally (intravenous, intramuscular, or subcutaneous), intracisternally, intravaginally, intraperitoneally, locally/topically (powders, ointments or drops), or as a buccal or nasal spray.

The compositions can be applied to the biological surface of hair by spraying or soaking, as well as by other techniques known to those skilled in the art. The compositions can be applied to plant tissue by spraying, soaking, soil drench, pre-emergence and post-emergence, as well as by other techniques known to those skilled in the art.

Compositions suitable for parenteral injection may comprise physiologically acceptable sterile aqueous or nonaqueous dispersions, suspensions or emulsions and sterile powders for reconstitution into sterile injectable solutions or dispersions. Examples of suitable aqueous and nonaqueous carriers, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate.

Proper fluidity can be maintained, for example, by the use of a coating such as lecithin, by the maintenance of the required particle size in the case of dispersions, and by the use of surfactants. The nanoparticulate compositions may also contain adjuvants, such as preserving, wetting, emulsifying, and dispersing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of an injectable pharmaceutical form can be brought about by the use of agents delaying absorption, such as aluminum monostearate and gelatin.

Solid dosage forms for oral administration of a pharmaceutical active agent include capsules, tablets, pills, powders, and granules. In such solid dosage forms, the active compound is admixed with at least one of the following: (a) one or more inert excipients (or carrier), such as dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid application forms include emulsions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual application levels of active ingredients in the nanoparticulate compositions of the invention may be varied to obtain an amount of active ingredient that is effective to obtain a desired response for a particular composition and method of application. The selected dosage level therefore depends upon the desired therapeutic effect, on the route of administration, on the desired duration of treatment, and other factors. In addition, the formulations of the present invention can be administered in combination with other pharmaceutical agents in the form of a solution, suspension, syrup or elixir or as formulated for solid dose administration.

The total daily amount of the active agent included in the inventive composition can be applied to a host in single or divided doses. Individuated units may contain such amounts of such submultiples thereof as may be used to make up the daily dose. It will be understood, however, that the specific dose level for any particular patient will depend upon a variety of factors, for example, when the host is a patient, such factors include the body weight, general health, sex, diet, time and route of administration, rates of absorption and excretion, combination with other drugs and the severity of the particular disease being treated.

The following examples are given to illustrate the present invention. It should be understood, however, that the invention is not to be limited to the specific conditions or details described in these examples.

EXAMPLE 1

The purpose of this example was to first prepare a nanoparticulate naproxen formulation comprising a cationic surface stabilizer, and second to compare the bioadhesive properties towards mucin of a nanoparticulate naproxen formulation comprising a non-ionic surface stabilizer and a nanoparticulate naproxen formulation comprising a cationic surface stabilizer. Naproxen is a crystalline compound used in anti-inflammatory, analgesic, and antipyretic applications.

A. Formulation Preparation

A first nanoparticulate formulation was prepared having a ratio of 30:3 naproxen (ALFA Co.) to polyvinylpyrrolidone (PVP) (BASF), which is a non-ionic surface stabilizer, and a second nanoparticulate formulation was prepared having a ratio of 10:1 naproxen to PMMTMABr (Polysciences Co.), which is a cationic surface stabilizer. The compositions were prepared by high-energy wet milling in a Dyno®-Mill (Willy Bachofen AG, Basel/Schweiz, Utengasse 15/17). In this process, the particle size of the naproxen is reduced in the presence of milling media and a surface stabilizer. The mill consisted of a 150 cc water-tight milling chamber which was jacket cooled to 10° C. The milling time ranged from 1–10 hours.

Each formulation was particle sized with a Horiba LA-910 particle analyzer (Horiba Instruments, Inc., Ann Arbor, Mich.). All sizing was performed in R.O. grade water. The particle sizes are given in Table 1.

TABLE 1

| Formulation | Mean Particle Size (nm) |
|---|---|
| Naproxen/PVP | 107 |
| Naproxen/PMMTMABr | 154 |

B. Sample Surface Preparation

For preparation of mucin-coated slide samples, freshly cleaved mica sheets were silanized with aminopropyltriethoxy silane (APTES) by placing the sheets in an air tight petri dish for several hours with a number of drops of APTES on the upper surface of the dish. After incubation in the APTES vapour, the mica sheets were incubated in a porcine mucin solution (Sigma Aldrich, St. Louis, Mo.), formulated in R.O. grade water, for a short period of time. The slides were then rinsed in R.O. grade water, again for a short period of time, to remove the excess mucin on the surface of the slide. The slides were then immediately used in the incubation studies to avoid drying or denaturing of the mucin functionality or protein structure.

C. Incubation and Sample Preparation for Imaging

A mucin coated slide was immersed in each of the naproxen formulations for 30 seconds (although the time of immersion is not critical). The sample was then rinsed in R.O. water and dried by capillary forces on an absorbent surface. The samples were left overnight to dry completely.

After the samples were dried they were adhered to scanning electron microscope (SEM) sample stubs with self adhesive conducting tape and gold coated. It was found that gold coating, using a Desk II cold sputter etch unit (Denton, Inc, Cherry Hill, N.J.) for 65 seconds, gave an adequate surface coating of gold to obtain good surface images.

D. Imaging and Results

Imaging was done with a Topcon SM510 SEM (Topcon Technologies, Inc., Pleasantville, Calif.). Imaging parameters, such as gun voltage and image size, were varied according to sample sensitivity and objective size. The extent of bioadhesion was determined through the relative surface coverage of the formulations on the various surfaces. The light areas apparent on the surface of the slides are attributed to adsorbed nanoparticulate composition.

A scanning electron micrograph of a mucin coated mica slide at a magnification of 2850×showed a smooth surface having no apparent features (FIG. 1). Thus, any absorbed entities within the imageable range of the SEM should be distinctly visualized on the mucin surface.

FIG. 2A shows a scanning electron micrograph of the interaction between mucin and a nanoparticulate naproxen formulation having PVP as a non-ionic surface stabilizer. The figure clearly shows the sporadic and inconsistent mucin coverage of the naproxen/PVP nanoparticulate composition. In contrast, FIG. 2B shows a scanning electron micrograph of the dramatically consistent, even, and extensive interaction between mucin and a nanoparticulate naproxen formulation having PMMTMABr as a cationic surface stabilizer. The images demonstrate that there are significantly greater light regions on the mucin-coated slide incubated with the nanoparticulate cationic surface stabilizer composition. This corresponds to increased activity of interaction between the mucin slide and the nanoparticulate naproxen/cationic stabilizer composition as compared to the nanoparticulate/non-ionic stabilizer composition. Moreover, the surface coverage of the nanoparticulate non-ionic stabilizer composition was significantly less homogeneous than the coverage observed with the nanoparticulate cationic stabilizer composition.

These results show that a nanoparticulate composition can be made utilizing a cationic surface stabilizer and a crystalline agent, and that such compositions exhibit increased bioadhesion to mucous as compared to conventional nanoparticulate compositions comprising a non-cationic surface stabilizer.

EXAMPLE 2

The purpose of this example was to compare the bioadhesive properties towards hair of a nanoparticulate naproxen formulation comprising a non-ionic surface stabilizer and a nanoparticulate naproxen formulation comprising a cationic surface stabilizer.

The naproxen formulations prepared in Example 1 were used in this example.

Hair samples were taken from a human subject's head immediately before incubation studies. The hair strands were rinsed in R.O. water before experimentation. The samples were prepared, incubated, and imaged as in Example 1.

Results

A scanning electron micrograph of a hair sample at a magnification of 2850×showed a flaky surface morphology. However, the surface was relatively clear of adventitious surface impurities that may detract from the overall surface coverage of the nanoparticulate formulations (FIGS. 3A and 3B).

FIGS. 4A and 4B show scanning electron micrographs of the interaction between hair and a nanoparticulate naproxen formulation having PMMTMABr as a surface stabilizer, and FIGS. 5A and 5B show scanning electron micrographs of the interaction between hair and a nanoparticulate naproxen formulation having PVP as a surface stabilizer. The lighter regions on the hair strand represent the adsorbed drug formulation. FIGS. 4A and 4B show large regions of the hair strand coated with the cationically stabilized nanoparticulate formulation, indicating a significant interaction between the cationically stabilized nanoparticulate formulation and the hair substrate. In contrast, FIGS. 5A and 5B show very little, if any, interaction between the hair strand and the non-ionically stabilized nanoparticulate formulation.

These results show that a nanoparticulate composition utilizing a cationic surface stabilizer and a crystalline agent exhibits increased bioadhesion to a hair substrate as compared to conventional nanoparticulate compositions comprising a non-cationic surface stabilizer.

EXAMPLE 3

The purpose of this example was to compare the bioadhesive properties towards plant tissue of a nanoparticulate naproxen formulation comprising a non-ionic surface. stabilizer and a nanoparticulate naproxen formulation comprising a cationic surface stabilizer.

The naproxen formulations prepared in Example 1 were used in this example.

A selection of plant tissues, including rose, geranium, hydrangea, clematis, honey suckle, and grape leaves, were analyzed with the SEM to determine the surface roughness. The hydrangea leaf was selected from this range due to its relative smoothness and the ability to visualize, with SEM, the adhered drug particles. The leaves were picked no more than two hours before investigation with the drug formulations. The leaves were rinsed in R.O. water immediately before the investigation. The samples were prepared, incubated, and imaged as in Example 1.

Results

A control SEM slide of plant tissue lacking any drug formulation is shown in FIGS. 6A and 6B.

FIGS. 7A and 7B show scanning electron micrographs of the interaction between plant tissue and a nanoparticulate naproxen formulation having PMMTMABr as a surface stabilizer, and FIGS. 8A and 8B show scanning electron micrographs of the interaction between plant tissue and a nanoparticulate naproxen formulation having PVP as a surface stabilizer. The lighter regions on the plant tissue represent the adsorbed drug formulation. The difference in adsorption activity between the cationically stabilized and non-ionically stabilized nanoparticulate formulations was slightly more difficult to determine for the plant tissue samples due to the relatively rough surface topography of the hydrangea leaf. However, FIGS. 7A and 7B show a mottled coverage of the plant tissue by the cationically stabilized nanoparticulate formulation, indicating an affinity of the formulation for the surface of the plant tissue. In contrast, FIGS. 8A and 8B show very little interaction between the non-ionic stabilized nanoparticulate formulation and the plant tissue.

These results show that a nanoparticulate composition utilizing a cationic surface stabilizer and a crystalline agent exhibits increased bioadhesion to plant tissue as compared to conventional nanoparticulate compositions comprising a non-cationic surface stabilizer.

EXAMPLE 4

The purpose of this example was to first prepare a nanoparticulate cyclosporine formulation comprising a cationic surface stabilizer, and second to compare the bioadhesive properties of a nanoparticulate cyclosporine formulation comprising an anionic and a non-ionic surface stabilizers and a nanoparticulate cyclosporine formulation comprising a cationic and a non-ionic surface stabilizers. Cyclosporine belongs to a group of non-polar cyclic oligopeptides that have immuosuppressant activity.

A. Formulation Preparation

An amorphous sample of cyclosporine was formulated into two nanoparticulate compositions. A first nanoparticulate cyclosporine formulation was prepared having non-ionic Plurionic® F88 (BASF, Inc.) and anionic sodium lauryl sulfate (SLS) (Spectrum Co.) as surface stabilizers, in ratios of 10:6:0.1 (drug:F88:SLS), and a second cationic nanoparticulate cyclosporine formulation was prepared having non-ionic Plurionic® F88 (BASF, Inc.) and cationic hexadecyltrimethyl ammonium bromide (HDMAB) (Sigma Co.) as surface stabilizers, in ratios of 10:6:0.05 (drug:F88:HDMAB). The formulations were prepared by high energy milling, as described in Example 1. The particle sizes, which were measured as described in Example 1, are given in Table 2.

TABLE 2

| Formulation | Mean Particle Size (nm) |
|---|---|
| Cyclosporine/F88/SLS | 172 |
| Cyclosporine/F88/HDMAB | 265 |

Mucin samples were prepared, incubated, and imaged as in Example 1.

B. Results

FIG. 9A shows a scanning electron micrograph of the interaction between mucin and nanoparticulate cyclosporine formulation containing an anionic stabilizer, and FIG. 9B shows a scanning electron micrograph of the interaction between mucin and a nanoparticulate cyclosporine formulation containing a cationic stabilizer. The lighter regions on the mucin represent the adsorbed drug formulation. FIG. 9B, showing the results of the cationically stabilized nanoparticulate composition, shows significantly greater lighter regions than FIG. 9A, showing the results of the anionically stabilized nanoparticulate composition. Moreover, adsorption to the mucin by the cationically stabilized nanoparticulate composition appears relatively homogeneous and consistent. In contrast, coverage of the mucin by the nanoparticulate anionically stabilized composition appears to be completely clear of the formulation.

These results show that a nanoparticulate composition can be made utilizing a cationic surface stabilizer and an amorphous agent, and that such compositions exhibit increased bioadhesion to mucous as compared to conventional nanoparticulate compositions comprising a non-cationic surface stabilizer.

EXAMPLE 5

The purpose of this example was to compare the bioadhesive properties towards hair of a nanoparticulate cyclosporine formulation comprising an anionic surface stabilizer and a nanoparticulate cyclosporine formulation comprising a cationic surface stabilizer.

The cyclosporine formulations prepared in Example 4 were used in this example.

The hair samples were prepared, incubated, and imaged as in Examples 1 and 2.

Results

FIGS. 10A and 10B show scanning electron micrographs of the interaction between a hair substrate and a nanoparticulate cyclosporine formulation having as surface stabilizers F88 and HDMAB, and FIGS. 11A and 11B show scanning electron micrographs of the interaction between a hair substrate and an nanoparticulate cyclosporine formulation having as surface stabilizers F88 and SLS. The lighter regions on the hair strand represent the adsorbed drug formulation.

FIGS. 10A and 10B show that the hair strand incubated with the cationically stabilized nanoparticulate composition is completely coated in a dense layer of the nanoparticulate matter. The underlying structure of the hair strand was completely masked by the adsorbed material. In contrast, FIGS. 11A and 11B show that the hair strand incubated with the anionically stabilized nanoparticulate composition appears to be completely clear of the formulation.

These results show that a nanoparticulate composition utilizing a cationic surface stabilizer and an amorphous agent exhibits increased bioadhesion to a hair substrate as compared to conventional nanoparticulate compositions comprising a non-cationic surface stabilizer.

EXAMPLE 6

The purpose of this example was to compare the bioadhesive properties towards plant tissue of a nanoparticulate cyclosporine formulation comprising an anionic surface stabilizer and a nanoparticulate cyclosporine formulation comprising a cationic surface stabilizer.

The cyclosporine formulations prepared in Example The plant tissue samples were prepared, incubated, and imaged as in Examples 1 and 3.

Results

FIG. 12A shows a scanning electron micrograph of the interaction between a hair substrate and a nanoparticulate cyclosporine formulation having F88 and SLS as surface stabilizers, and FIG. 12B shows a scanning electron micrograph of the interaction between a hair substrate and a nanoparticulate cyclosporine formulation having F88 and HDMAB as surface stabilizers. The lighter regions on the plant tissue represent the adsorbed drug formulation. As with hair and mucin, the cationically stabilized nanoparticulate cyclosporine formulation achieved greater coverage of the plant tissue than the anionically stabilized cyclosporine formulation.

The fibril morphology of the plant tissue in FIGS. 12A and 12B is attributed to the extent of dehydration of the sample while it was gold coated. The striated, fibril like morphology became increasingly visible when the plant tissue became more dehydrated. However, this difference in morphology did not alter the results of the experiment.

These results show that a nanoparticulate composition utilizing a cationic surface stabilizer and an amorphous agent exhibits increased bioadhesion to plant tissue as compared to conventional nanoparticulate compositions comprising a non-cationic surface stabilizer.

EXAMPLE 7

The purpose of this example was to first prepare a nanoparticulate triamcinolone acetonide (TA) formulation comprising a cationic surface stabilizer, and second to compare the bioadhesive mucin properties of a nanoparticulate TA formulation comprising an anionic surface stabilizer and a nanoparticulate TA formulation comprising a cationic surface stabilizer. TA is a crystalline glucocorticosteroid that has anti-inflammatory and anti-asthmatic (inhalent) properties.

A. Formulation Preparation

A first nanoparticulate TA formulation was prepared having hydroxypropylcellulose SL grade (HPC-SL) (NISSO Chemicals, Inc.) and SLS (Spectrum Co.) as surface stabilizers, in ratios of 5:1:0.01 (drug:HPC-SL:SLS), and a second nanoparticulate TA formulation was prepared having HPC-SL and benzalkonium chloride (BKC) (Spectrum, Co.) as surface stabilizers, in ratios of 5:1:0.05 (drug:HPC-SL:BKC). The formulations were prepared by high energy milling, as described in Example 1. The particle sizes, which were measured as described in Example 1, are given in Table 3.

TABLE 3

| Formulation | Mean Particle Size (nm) |
| --- | --- |
| TA/HPC-SL/SLS | 269 |
| TA/HPC-SL/BKC | 369* |

*The particle size measurements of the TA/HPC-SL/BKC formulation were taken in 0.01% BKC solution.

Mucin samples were prepared, incubated, and imaged as in Example 1.

B. Results

FIG. 13A shows a scanning electron micrograph of the interaction between mucin and an anionically stabilized nanoparticulate TA formulation, and FIG. 13B shows a scanning electron micrograph of the interaction between mucin and a cationically stabilized nanoparticulate TA formulation. The lighter regions on the mucin represent the adsorbed drug formulation. The cationically stabilized nanoparticulate TA formulation exhibited significant adhesion to the mucin slide, in which the composition almost completely covered the mucin (see FIG. 13B). In contrast, the anionically stabilized nanoparticulate TA formulation exhibited minimal sporadic coverage of the mucin slide (see FIG. 13A).

These results show that a nanoparticulate composition can be made utilizing a cationic surface stabilizer and a crystalline agent, and that such compositions exhibit increased bioadhesion to mucous as compared to conventional nanoparticulate compositions comprising a non-cationic surface stabilizer.

EXAMPLE 8

The purpose of this example was to compare the bioadhesive properties towards hair of a nanoparticulate TA formulation comprising an anionic surface stabilizer and a nanoparticulate TA formulation comprising a cationic surface stabilizer.

The TA formulations prepared in Example 7 were used in this example.

The hair samples were prepared, incubated, and imaged as in Examples 1 and 2.

Results

FIGS. 14A and 14B show scanning electron micrographs of the interaction between a hair substrate and an anionically stabilized nanoparticulate TA formulation having HPC-SL and SLS as surface stabilizers, and FIGS. 15A and 15B show scanning electron micrographs of the interaction between a hair substrate and a cationically stabilized nanoparticulate TA formulation having HPC-SL and BKC as surface stabilizers. The lighter regions on the hair strand represent the adsorbed drug formulation.

FIGS. 15A and 15B show that the hair strand incubated with the cationically stabilized nanoparticulate composition is completely coated in a dense layer of the nanoparticulate matter. The underlying structure of the hair strand was completely masked by the adsorbed material. In contrast, FIGS. 14A and 14B show that the hair strand incubated with the anionically stabilized nanoparticulate composition appears to be almost completely clear of the formulation.

These results show that a nanoparticulate composition utilizing a cationic surface stabilizer and a crystalline agent exhibits increased bioadhesion to a hair substrate as compared to conventional nanoparticulate compositions comprising a non-cationic surface stabilizer.

EXAMPLE 9

The purpose of this example was to first prepare a nanoparticulate formulation comprising a cationic surface stabilizer and benzoic acid, 3,5-bis(acetylamino) 2,4,6-triodo-, 4-(ethyl-3-ethoxy-2-butenoate) ester (WIN68209), and second to compare the bioadhesive properties towards skin of a nanoparticulate WIN68209 formulation comprising a non-ionic surface stabilizer and a nanoparticulate WIN68209 formulation comprising a cationic surface stabilizer. WIN68209 is an crystalline X-ray imaging agent for interstitial cavities. The compound is insoluble in water.

A. Formulation Preparation

A non-ionically stabilized nanoparticulate WIN68209 formulation was prepared having Plurionic® F108 (BASF, Inc.) as a surface stabilizer, in a ratio of 5:1 (drug:F108), and a cationically stabilized nanoparticulate WIN68209 formulation was prepared having polyvinylpyrrolidone-2- dimethylaminoethyl methacrylate dimethyl sulfate (PVPDMAEM) (Polysciences, Inc.) as a surface stabilizer, in a ratio of 5:1 (drug:PVPDMAEM). The formulations were prepared by high energy milling, as described in Example 1. The particle sizes, which were measured as described in Example 1, are given in Table 4.

TABLE 4

| Formulation | Mean Particle Size (nm) |
| --- | --- |
| WIN68209/F108 | 181 |
| WIN68209/PVPDMAEM | 200 |

This formulation was used to test bioadhesiveness to skin due to its high degree of insolubility. The human allograft was extremely hydrated when used and the drying regime was extensive and slow. Thus, less insoluble drugs would have been difficult to visualize with the SEM.

B. Sample Preparation

Human allograft was obtained from the Ohio Valley Tissue and Skin Center (Cincinnati, Ohio). The allograft was stored packed in dry ice at a temperature of less than −70° C. Before use, the skin was rapidly thawed (within five minutes) in R.O. water maintained at 35–40° C. The allograft was then rinsed in R.O. water and immediately used for the incubation trials. FIGS. 16A and 16B show a scanning electron micrographs of human allograft skin prior to exposure to a hanoparticulate drug formulation.

C. Results

FIGS. 17A and 17B show scanning electron micrographs of the interaction between human allograft and a nonionically stabilized nanoparticulate WIN68209 formulation, and FIGS. 18A and 18B show scanning electron micrographs of the interaction between human allograft and a cationically stabilized nanoparticulate WIN68209 formulation. The lighter regions on the human allograft represent the adsorbed drug formulation. FIGS. 18A and 18B, showing the results of the cationically stabilized nanoparticulate composition, have significantly greater lighter regions than FIGS. 17A and 17B, showing the results of the non-ionically stabilized nanoparticulate composition. This greater light region corresponds to significantly greater drug adsorption to human allograft by the cationically stabilized composition as compared to the non-ionically stabilized composition.

These results show that a nanoparticulate composition can be made utilizing a cationic surface stabilizer, and that such compositions exhibit increased bioadhesion to skin as compared to conventional nanoparticulate compositions comprising a non-cationic surface stabilizer.

EXAMPLE 10

The purpose of this example was to first prepare a formulation comprising of unmilled naproxen (about 22 µm) and a cationic surface stabilizer, and second to compare the bioadhesive properties towards mucin of an unmilled naproxen formulation comprising a cationic stabilizer and an unmilled naproxen formulation comprising a non-ionic surface stabilizer.

A. Formulation Preparation

A first formulation was prepared having a ratio of 10:1 naproxen to PMMTMABr (Polysciences Co.), and a second formulation was prepared having a ratio of 30:3 naproxen (ALFA Co.) to polyvinylpyrrolidone (PVP) (BASF). The compositions were prepared by mixing raw drug with either the cationic (PMMTMABr) or non-ionic (PVP) surfactant. The naproxen had a particle size of about 22 µm.

B. Results

FIG. 19A shows a scanning electron micrograph of the interaction between mucin and the unmilled naproxen formulation having PMMTMABr as a surface stabilizer. The figure clearly shows the lack of mucin coverage by the naproxen/cationic PMMTMABr unmilled composition. Analogously, FIG. 19B shows a scanning electron micrograph of interaction between mucin and the naproxen formulation having PVP as a surface stabilizer.

The images demonstrate that size of the active agent particles is a critical factor in the ability of the formulations to exhibit bioadhesive properties, as the unmilled compositions exhibited minimal, if any, bioadhesiveness to the mucin.

EXAMPLE 11

The purpose of this example was to compare the bioadhesive properties towards hair of an unmilled naproxen formulation comprising a cationic stabilizer and an unmilled naproxen formulation comprising an non-ionic stabilizer.

The formulations prepared in Example 10 were used in this example.

Results

FIGS. 20A and 20B show scanning electron micrographs of the interaction between hair and an unmilled naproxen formulation having PMMTMABr as a surface stabilizer at 500× and 2850×magnification, respectively. The figures clearly show the lack of hair coverage by the cationically stabilized naproxen/PMMTMABr composition. Similarly, FIGS. 21A and 21B show scanning electron micrographs of the interaction between hair and an unmilled naproxen formulation having PVP as a surface stabilizer at 500× and 2850×magnification, respectively. Again, the figures clearly show the lack of coverage on hair by the naproxen/non-ionic PVP formulation.

The images demonstrate that size of the active agent particles is a critical factor in the ability of the formulations to exhibit bioadhesive properties on hair coated with the unmilled naproxen cationic surface stabilizer composition. An unmilled composition exhibits minimal, if any, bioadhesive properties when combined with a cationic or non-ionic surfactant. These results indicate that, in addition to the charge of the surface active agent, the size of the active agent particles are important to the bioadhesive properties of the active agent/surfactant compositions.

EXAMPLE 12

The purpose of this example was to compare the bioadhesive properties towards plant tissue of an unmilled naproxen formulation comprising a non-ionic stabilizer, and an unmilled naproxen formulation comprising a cationic stabilizer.

The formulations prepared in Example 10 were used in this example.

Results

FIGS. 22A and 22B show scanning electron micrographs of the interaction between plant tissue and unmilled naproxen formulations having PMMTMABr and PVP as surface stabilizers, respectively. The figures show the lack of coverage on plant tissue by the naproxen/PMMTMABr and naproxen/PVP compositions.

The images demonstrate that size of the active agent particles is a critical factor in the ability of the formulations to exhibit bioadhesive properties.

EXAMPLE 13

The purpose of this example was to first prepare micronized (about 6 μm) formulations comprising naproxen and a cationic surface stabilizer and naproxen and a non-ionic surface stabilizer, and second to compare the bioadhesive properties towards mucin of the micronized naproxen formulation comprising a cationic stabilizer with the micronized naproxen formulation comprising a non-ionic surface stabilizer.

A. Formulation Preparation

A first micronized formulation was prepared having a ratio of 10:1 naproxen to PMMTMABr (Polysciences Co.), and a second micronized formulation was prepared having a ratio of 30:3 naproxen (ALFA Co.) to polyvinylpyrrolidone (PVP) (BASF). The micronized drug particles were prepared with standard jet milling procedures which produced a resultant final particle size of about 6 microns.

B. Results

FIG. 23A shows a scanning electron micrograph of the interaction between mucin and the micronized naproxen/PMMTMABr formulation. Analogously, FIG. 23B shows a scanning electron micrograph of interaction between mucin and the micronized naproxen/PVP formulation. The figures clearly show minimal bioadhesion to mucin by the cationically stabilized naproxen/PMMTMABr micronized composition and negligible bioadhesion by the non-ionically stabilized naproxen/PVP micronized formulation. The images demonstrate that size of the active agent particles, in addition to the charge of the surface stabilizer, is a factor in the ability of the formulations to exhibit bioadhesive properties to mucin. Moreover, these results show that a micronized composition exhibits minimal bioadhesive properties.

EXAMPLE 14

The purpose of this example was to compare the bioadhesive properties towards hair of a micronized naproxen formulation comprising a cationic stabilizer and a micronized naproxen formulation comprising an non-ionic surface stabilizer.

The formulations prepared in Example 13 were used in this example.

Results

FIGS. 24A and 24B show scanning electron micrographs of the interaction between hair and a micronized naproxen/PMMTMABr formulation at 500× and 2850×magnification, respectively. Analogously, FIGS. 25A and 25B show scanning electron micrographs of interaction between hair and a non-ionic micronized naproxen/PVP formulation at 500× and 2850×magnification, respectively. The figures show minimal coverage of the hair by the cationically stabilized naproxen/PMMTMABr micronized composition and negligible coverage by the non-ionically stabilized micronized naproxen/PVP composition.

The images demonstrate that size of the active agent particles, in addition to the charge of the surface stabilizer, is a critical factor in the ability of the formulations to exhibit bioadhesive properties, as the micronized (about 6 μm) compositions exhibited minimal bioadhesive properties.

EXAMPLE 15

The purpose of this example was to compare the bioadhesive properties towards plant tissue of a micronized naproxen formulation comprising a cationic stabilizer with micronized naproxen formulation comprising a non-ionic stabilizer.

The formulations prepared in Example 13 were used in this example.

Results

FIG. 26A shows a scanning electron micrograph of the interaction between plant tissue and a micronized naproxen/PMMTMABr formulation at 1000×magnification. FIG. 26B shows a scanning electron micrograph of the interaction between plant tissue and a non-ionic micronized naproxen/PVP formulation at 1000×magnification. The figures indicate minimal coverage on the plant tissue by the cationically stabilized naproxen/PMMTMABr micronized composition and negligible coverage by the non-ionically stabilized micronized naproxen/PVP formulation.

The images demonstrate that size of the active agent particles, in addition to the charge of the stabilized, is a critical factor in the ability of the formulations to exhibit bioadhesive properties.

Throughout the specification, any and all references to publicly available documents are specifically incorporated by reference. It will be apparent to those skilled in the art that various modifications and variations can be made in the methods and compositions of the present invention without departing from the spirit or scope of the invention. Thus, it is intended that the present invention cover the modifications and variations of this invention, provided they come within the scope of the appended claims and their equivalents.

What is claimed is:

1. A stable bioadhesive nanoparticulate composition comprising:
    (a) active agent particles in a semi-crystalline state, an amorphous state, a mixture of crystalline and semi-crystalline, a mixture of crystalline and amorphous, or a mixture of crystalline, semi-crystalline, and amorphous; and
    (b) adsorbed to the surface thereof at least one cationic surface stabilizer, wherein the active agent particles have an effective average particle size of less than about 4000 nm, wherein the nanoparticulate composition adsorbs to a biological surface, and wherein the nanoparticulate composition does not contain solvent residues resulting from solvent extraction or solvent precipitation.

2. The composition of claim 1, wherein the active agent is selected from the group consisting of a poorly water-soluble active agent and a water-soluble active agent.

3. The composition of claim 1, wherein the active agent is selected from the group consisting of a drug, vitamin, herb, cosmetic agent, coloring agent, flavor agent, fragrance agent, sunscreen, moisturizer, deodorant, food product, hair conditioner agent, hair dye, hair spray agent, hair cosmetic agent, hair cleanser agent, depilatory agent, insecticide, fertilizer, pesticide, herbicide, germicide, and plant growth regulating agent.

4. The composition of claim 3, wherein the drug is selected from the group consisting of proteins, peptides, nutriceuticals, anti-obesity agents, corticosteroids, elastase inhibitors, analgesics, anti-fungals, oncology therapies, antiemetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, blood products and substitutes, cardiac inotropic agents, contrast media, cough suppressants, diagnostic agents, diagnostic imaging agents, diuretics, dopaminergics, haemostatics, immunological agents, lipid regulating agents, muscle relaxants, parasympathomimetics, parathyroid calcitonin and biphosphonates, prostaglandins, radio-pharmaceuticals, sex hormones, anti-allergic agents, stimulants and anoretics, sympathomimetics, thyroid agents, vasodilators, xanthines, acne medication, alpha-hydroxy formulations, cystic-fibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, and respiratory illness therapies associated with acquired immune deficiency syndrome.

5. The composition of claim 1, wherein the composition is formulated for administration selected from the group consisting of vaginal, ocular, nasal, buccal, oral, colonic, topical, and subcutaneous administration.

6. The composition of claim 1, wherein the at least one cationic surface stabilizer is selected from the group consisting of a polymer, a biopolymer, a polysaccharide, a cellulosic, an alginate, a nonpolymeric compound, and a phospholipid.

7. The composition of claim 1, wherein the surface stabilizer is selected from the group consisting of benzalkonium chloride, polymethylmethacrylate trimethylammonium bromide, polyvinylpyrrolidone-2-dimethylaminoethyl methacrylate dimethyl sulfate, and hexadecyltrimethyl ammonium bromide.

8. The composition of claim 1, wherein the effective average particle size of the agent particles is less than about 3500 nm.

9. The composition of claim 1, wherein the composition further comprises one or more pharmaceutically acceptable excipients.

10. A stable bioadhesive nanoparticulate composition comprising:
 (a) active agent particles in a semi-crystalline state, an amorphous state, a mixture of crystalline and semi-crystalline, a mixture of crystalline and amorphous, or a mixture of crystalline, semi-crystalline, and amorphous, wherein the active agent particles are present in an amount of about 99.99 to 0.01(w/w) based on the total weight of the composition; and
 (b) adsorbed to the surface thereof at least one cationic surface stabilizer,
wherein the active agent particles have an effective average particle size of less than about 4000 nm, and wherein the nanoparticulate composition adsorbs to a biological surface.

11. A stable bioadhesive nanoparticulate composition comprising:
 (a) active agent particles in a semi-crystalline state, an amorphous state, a mixture of crystalline and semi-crystalline, a mixture of crystalline and amorphous, or a mixture of crystalline, semi-crystalline, and amorphous; and
 (b) adsorbed to the surface thereof at least one cationic surface stabilizer, wherein the surface stabilizer is present in an amount of about 0.001 to about 99.999% (w/w) based on the total weight of the composition,
wherein the active agent particles have an effective average particle size of less than about 4000 nm, and wherein the nanoparticulate composition adsorbs to a biological surface.

12. The composition of claim 1, wherein the composition adsorbs to a biological surface selected from the group consisting of an insect, teeth, bone, nails, chitin, feathers, scales, mucous, skin, hair, and plant tissue.

13. The composition of claim 1 in a dry powder form.

14. The composition of claim 1, wherein the effective average particle size of the agent particles less than about 3000 nm.

15. The composition of claim 1, wherein the effective average particle size of the agent particles is less than about 2500 nm.

16. The composition of claim 1, wherein the effective average particle size of the agent particles is less than about 2000 nm.

17. The composition of claim 1, wherein the effective average particle size of the agent particles is less than about 1500 nm.

18. The composition of claim 1, wherein the effective average particle size of the agent particles is less than about 1000 nm.

19. The composition of claim 1, wherein the effective average particle size of the agent particles is less than about 800 nm.

20. The composition of claim 1, wherein the effective average particle size of the agent particles is less than about 700 nm.

21. The composition of claim 1, wherein the effective average particle size of the agent particles is less than about 600 nm.

22. The composition of claim 1, wherein the effective average particle size of the agent particles is less than about 400 nm.

23. The composition of claim 1, wherein the effective average particle size of the agent particles is less than about 300 nm.

24. The composition of claim 1, wherein the effective average particle size of the agent particles is less than about 250 nm.

25. The composition of claim 1, wherein the effective average particle size of the agent particles is less than about 200 nm.

26. The composition of claim 1, wherein the effective average particle size of the agent particles is less than about 100 nm.

27. The composition of claim 1, wherein the effective average particle size of the agent particles is less than about 50 nm.

* * * * *